United States Patent [19]

Goulet et al.

[11] Patent Number: 5,310,903

[45] Date of Patent: May 10, 1994

[54] IMIDAZOLIDYL RAPAMYCIN DERIVATIVES

[75] Inventors: Mark Goulet, Westfied; William H. Parsons, Edison; Matthew J. Wyvratt, Mountainside, all of N.J.

[73] Assignee: Merck & Co., Inc., Rahway, N.J.

[21] Appl. No.: 26,925

[22] Filed: Mar. 5, 1993

[51] Int. Cl.$^5$ .................. C07D 498/18; A61K 31/395
[52] U.S. Cl. .................................................. 540/456
[58] Field of Search ........................................ 546/456

[56] References Cited

U.S. PATENT DOCUMENTS

| | | | |
|---|---|---|---|
| 3,929,992 | 12/1975 | Sehgal et al. | 424/122 |
| 4,650,803 | 3/1987 | Stella et al. | 514/291 |
| 5,100,883 | 3/1992 | Schiehser | 514/183 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,725 | 6/1992 | Kao et al. | 514/183 |
| 5,120,727 | 6/1992 | Kao et al. | 514/183 |
| 5,120,842 | 6/1992 | Failli et al. | 540/452 |
| 5,138,051 | 8/1992 | Hughes et al. | 540/456 |
| 5,151,413 | 9/1992 | Caufield et al. | 514/63 |
| 5,162,333 | 11/1992 | Failli et al. | 514/291 |
| 5,162,334 | 11/1992 | Goulet et al. | 514/291 |
| 5,169,851 | 12/1992 | Hughes et al. | 514/291 |

FOREIGN PATENT DOCUMENTS

| | | | |
|---|---|---|---|
| 0227355 | 7/1987 | European Pat. Off. | 540/456 |
| 0516347 | 12/1992 | European Pat. Off. | 540/456 |
| 2245891 | 1/1992 | United Kingdom | 540/456 |
| WO89/05304 | 6/1989 | World Int. Prop. O. | 540/456 |
| WO91/02736 | 3/1991 | World Int. Prop. O. | 540/456 |
| WO91/13889 | 9/1991 | World Int. Prop. O. | 540/456 |
| WO92/05179 | 4/1992 | World Int. Prop. O. | 540/456 |
| WO92/14737 | 9/1992 | World Int. Prop. O. | 540/456 |
| WO92/20688 | 11/1992 | World Int. Prop. O. | 540/456 |
| WO92/21341 | 12/1992 | World Int. Prop. O. | 540/456 |
| WO93/05058 | 3/1993 | World Int. Prop. O. | 540/456 |
| WO93/05059 | 3/1993 | World Int. Prop. O. | 540/456 |

OTHER PUBLICATIONS

Findlay, et al., *Can. J. Chem.*, 58, 579–590 (1980).

*Primary Examiner*—Robert T. Bond
*Attorney, Agent, or Firm*—Charles M. Caruso; J. Eric Thies

[57] ABSTRACT

Imidazolidyl rapamycin derivatives of the general structural Formula I:

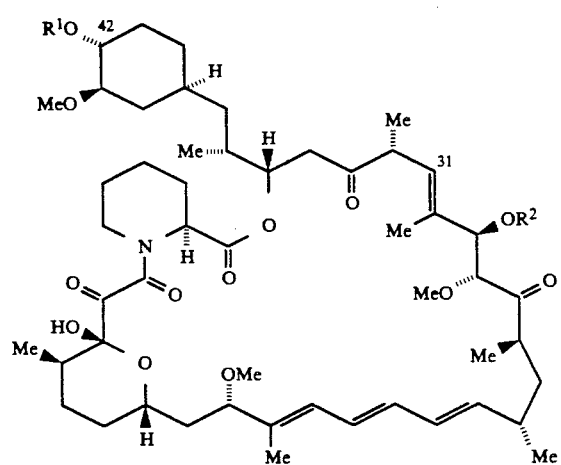

have been prepared from suitable precursors by alkylation and/or arylation at C-42 and/or C-31. These compounds are useful in a mammalian host for the treatment of autoimmune diseases and diseases of inflammation, infectious diseases, the prevention of rejection of foreign organ transplants and the treatment of solid tumors.

5 Claims, No Drawings

IMIDAZOLIDYL RAPAMYCIN DERIVATIVES

SUMMARY OF THE INVENTION

The present invention is related to imidazolidyl rapamycin derivatives which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis, and glomerulonephritis), diseases of inflammation, infectious diseases (particularly fungal infections), the prevention of rejection of foreign organ transplants, e.g. bone marrow, kidney, liver, heart, skin, small-bowel, and pancreatic-islet-cell transplants, and the treatment of solid tumors.

More particularly, this invention relates to compounds of the general structural Formula I:

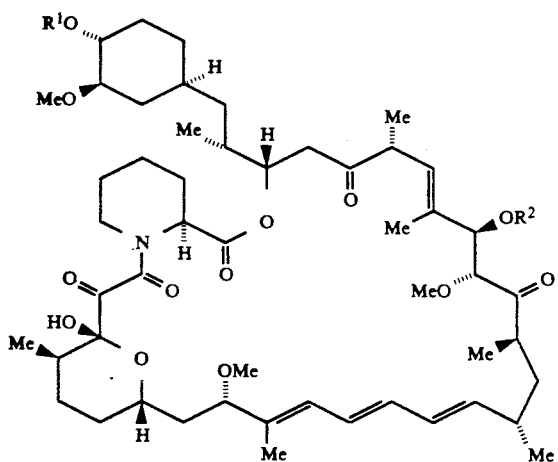

wherein $R^1$ and $R^2$ are hereinafter defined.

This invention also relates to pharmaceutical compositions containing the compounds, and to a method of use of the present compounds and other agents for the treatment and prevention of certain afflictions, diseases and illnesses.

BACKGROUND OF THE INVENTION

Rapamycin characterized by Findlay and co-workers in 1978 is a 35-membered macrolide isolated from *S. hygroscopicus* (*Can. J. Chem.*, 1978, 56, 2491, *J. Antibiotics*, 1975, 28, 721, U.S. Pat. No. 3,929,992, issued Dec. 30, 1975, U.S. Pat. No. 3,993,749, issued Nov. 23, 1975. Rapamycin has been found to have antifungal activity, particularly against *Candida albicans*, both in vitro and in vivo (*J. Antibiotics*, 1978, 31, 539).

Rapamycin alone (U.S. Pat. No. 4,885,171) or in combination with picibanil (U.S. Pat. No. 4,401,653) has been shown to have antitumor activity. R. Martel et al. (*Can. J. Physiol. Pharmacol*, 55, 48 (1977) disclosed that rapamycin is effective in an experimental allergic encephalomyelitis model, a model for multiple sclerosis; in an adjuvant arthritis model, a model for rheumatoid arthritis; and effectively inhibited the formation of IgE-like antibodies.

The immunosuppressive effects of rapamycin have been disclosed (*FASEB* 3, 3411 (1989); *Med. Sci. Res.*, 1989, 17, 877). Cyclosporin A and FK-506, other macrocyclic molecules, also have been shown to be effective as immunosuppressive agents, therefore useful in preventing transplant rejection (*FASEB* 3, 3411 (1989); *FASEB* 3, 5256 (1989); and *Lancet* 1183 (1978)).

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthitis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmul. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117), multidrug resistance (M. Naito, et al., *Cancer Chemoether. Pharmacol.*, 1992, 29, 195–200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

Mono- and diacylated derivatives of rapamycin (esterified at the 31 and 42 positions) have been shown to be useful as antifungal agents (U.S. Pat. No. 4,316,885) and have been used as water soluble prodrugs of rapamycin (U.S. Pat. No. 4,650,803 and PCT Patent Publication WO 92/21341). Reduction products of rapamycin have been prepared (U.S. Pat. Nos. 5,102,876 and 5,138,051). Derivatives of rapamycin at the 31 and 42 positions which have been disclosed include: carboxylic acid esters (PCT Patent Publication WO92/05179); carbamates (U.S. Pat. No. 5,118,678); amide esters (U.S. Pat. No. 5,118,677); fluorinated esters (U.S. Pat. No. 5,100,883); acetals (U.S. Pat. No. 5,151,413); and silyl ethers (U.S. Pat. No. 5,120,842). In addition, bicyclic derivatives of rapamycin connected via the 31, 42 positions (U.S. Pat. No. 5,120,725) and rapamycin dimers connected via the 42 position (U.S. Pat. No. 5,120,727) have been disclosed. Various aryl(lower alkyl) and heteroaryl derivatives of FK-506 type compounds have also been disclosed (UK Patent Publication No. GB 2,245,891A). O-Aryl, O-alkyl, O-alkenyl and O-alkynyl derivatives of FK-506 type compounds have been disclosed (EPO Patent Publication No. 0,515,071).

DETAILED DESCRIPTION OF THE INVENTION

A. Scope of the Invention

The novel compound of this invention has structural Formula I:

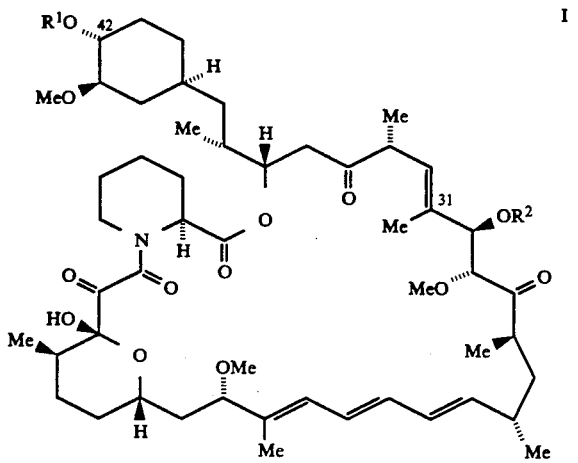

or a pharmaceutically acceptable salt thereof, wherein:
$R^1$ is selected from:

(1) 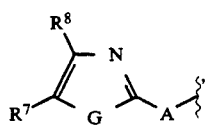

wherein G is N—$R^6$, O, S, SO, or $SO_2$, (2) 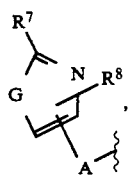

(3) 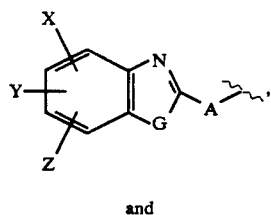

and (4) 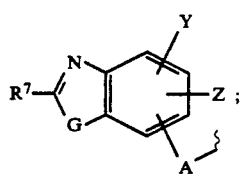

$R^2$ is independently selected from:
(1) the definitions of $R^1$;
(2) hydrogen;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl;
(8) substituted biphenyl in which the substituents are X, Y and Z;
(9) $C_{1-10}$alkyl;
(10) substituted $C_{1-10}$alkyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are independently selected from:
    (i) hydrogen, or
    (ii) $C_{1-6}$alkyl unsubstituted or substituted with one or more of the substituent(s) selected from:
      (a') phenyl, which may be substituted with X, Y and Z,
      (b') —OH,
      (c') $C_{1-6}$alkoxy,
      (d') —$CO_2H$,
      (e') —$CO_2$-$C_{1-6}$alkyl,
      (f') —$C_{3-7}$cycloalkyl, and
      (g') —$OR^{11}$,
    (iii) or where $R^9$ and $R^{10}$ and the N to which they are attached may form an unsubstituted or substituted 3-7-membered heterocyclic ring which may include one or two additional heteroatoms independently selected from the group consisting of O, $S(O)_p$, $NR^{19}$, wherein $R^{19}$ is hydrogen or $C_{1-6}$alkyl unsubstituted or substituted by phenyl, and p is 0, 1 or 2, such as morpholine, thiomorpholine, piperidine, or piperizine,
  (h) —$NR^9CO$—$C_{1-6}$alkyl-$R^{10}$, wherein $R^9$ and $R^{10}$ are as defined above,
  (i) —$COOR^9$, wherein $R^9$ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —$OR^{11}$, and
  (r) —$S(O)_p$—$C_{1-6}$alkyl;
(11) $C_{3-10}$alkenyl;
(12) substituted $C_{3-10}$alkenyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are as defined above, (h) —NR$^9$CO—C$_{1-6}$alkyl, wherein R$^9$ is as defined above,
(i) —COOR$^9$, wherein R$^9$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z;
(q) —OR$^{11}$, and
(r) —S(O)$_p$—C$_{1-6}$alkyl;
(13) C$_{3-10}$alkynyl;
(14) substituted C$_{3-10}$alkynyl in which one or more substituents(s) is(are) selected from:
(a) hydroxy,
(b) oxo,
(c) C$_{1-6}$alkoxy,
(d) phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^9$R$^{10}$, wherein R$^9$ and R$^{10}$ are as defined above,
(h) —NR$^9$CO—C$_{1-6}$alkyl, wherein R$^9$ is as defined above,
(i) —COOR$^9$, wherein R$^9$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z, and
(q) —OR$^{11}$; and
(15) —R$^{11}$;
R$^6$ is selected from the group consisting of:
(1) hydrogen,
(2) C$_{1-6}$alkyl, unsubstituted or substituted with:
(a) hydroxy
(b) C$_{1-6}$alkoxy,
(c) —NR$^{12}$R$^{13}$, wherein R$^{12}$ and R$^{13}$ are independently selected from
(i) hydrogen,
(ii) C$_{1-6}$alkyl, or
(iii) C$_{3-6}$alkenyl,
(d) phenyl, unsubstituted or substituted with X, Y and Z,
(e) —OR$^{11}$,
(3) C$_{3-6}$alkenyl, unsubstituted or substituted with:
(a) hydroxy,
(b) phenyl, unsubstituted, or substituted with X, Y and Z, or
(c) C$_{1-6}$alkoxy,
(4) phenyl, unsubstituted or substituted with X, Y and Z,
(5) —R$^{11}$,
(6) X, Y or Z;
R$^7$ and R$^8$ independently are selected from the group consisting of:
(1) hydrogen,
(2) C$_{1-7}$alkyl,
(3) C$_{2-6}$alkenyl,
(4) —(CH$_2$)$_m$—NR$^9$R$^{10}$, wherein R$^9$ and R$^{10}$ are as defined above, and m is 0, 1, 2, or 3
(5) —CF$_3$,
(6) —CONR$^9$R$^{10}$, wherein R$^9$ and R$^{10}$ are as defined above,
(7) R$^{14}$O(CH$_2$)$_m$—wherein R$^{14}$ is hydrogen, C$_{1-6}$alkyl, hydroxy—C$_{2-3}$alkyl, —CF$_3$, phenyl, R$^{11}$ or naphthyl and m is as defined above,
(8)

$$R^{14}OC(CH_2)_m-\overset{\overset{\text{O}}{\|}}{}$$

wherein R$^{14}$ and m are as defined above;
(9) phenyl—(CH$_2$)$_m$—wherein m is as defined above and the phenyl is unsubstituted or substituted with X, Y and Z,
(10) naphthyl—(CH$_2$)$_m$—wherein m is as defined above and the naphthyl is unsubstituted or substituted with X, Y and Z,
(11) biphenyl—(CH$_2$)$_m$—wherein m is as defined above and the biphenyl is unsubstituted or substituted with X, Y and Z,
(12) heteroaryl—(CH$_2$)$_m$—wherein m is as defined above and the heteroaryl is unsubstituted or substituted with X, Y and Z,
(13) morpholinyl, and
(14) —CH=CH—phenyl wherein the phenyl is unsubstituted or substituted with X, Y and Z;
R$^{11}$ is selected from:
(a) —PO(OH)O$^-$M$^+$, wherein M$^+$ is a positively charged inorganic or organic counterion,
(b) —SO$_3$$^-$M$^+$,
(c) —CO(CH$_2$)$_q$CO$_2$$^-$M$^+$, wherein q is 1 to 3, and
(d) —CO—C$_{1-6}$alkyl—NR$^9$R$^{10}$, wherein R$^9$ and R$^{10}$ are as defined above and the alkyl is unsubstituted or substituted with one or more substituents selected from:
(i) hydrogen,
(ii) C$_{1-6}$alkoxy,
(iii) —NR$^{12}$R$^{13}$, wherein R$^{12}$ and R$^{13}$ are as defined above,
(iv) —COOR$^6$, wherein R$^6$ is as defined above,
(v) phenyl,
(iv) substituted phenyl in which the substituents are X, Y and Z,
(vii) heteroaryl,
(viii) —SH, and
(ix) —S—C$_{1-6}$alkyl;
A is selected from the group consisting of:
(1) a bond,
(2) C$_{1-10}$alkyl;
(3) substituted C$_{1-10}$alkyl in which one or more substituent(s) is(are) selected from:
(a) hydroxy,
(b) oxo,
(c) C$_{1-6}$alkoxy,
(d) phenyl—C$_{1-3}$alkoxy,
(e) substituted phenyl—C$_{1-3}$alkoxy, in which the substituents on phenyl are X, Y and Z,
(f) —OCO—C$_{1-6}$alkyl,
(g) —NR$^9$R$^{10}$, wherein R$^9$ and R$^{10}$ are as defined above,
(h) —NR$^9$CO—C$_{1-6}$alkyl, wherein R$^9$ is as defined above,
(i) —COOR$^9$, wherein R$^9$ is as defined above, (j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$, and
(r) —S(O)$_p$—C$_{1-6}$alkyl;
(4) —C$_{1-10}$alkyl wherein one or more of the alkyl carbons is replaced by a group selected from: —NR$^9$—, —O—, —S(O)$_n$—, —CO$_2$—, —O$_2$C—, —CONR$^9$—, —NR$^9$CO—, —NR$^9$CONR$^{10}$—;
(5) —C$_{1-10}$alkenyl wherein alkenyl contains one to four double bonds and wherein one or more of the alkyl carbons is replaced by a group selected from: —NR$^9$—, —O—, —S(O)$_p$—, —O$_2$C—, —CONR$^9$—, —NR$^9$CO—, and —NR$^9$CONR$^{10}$—;
(6)

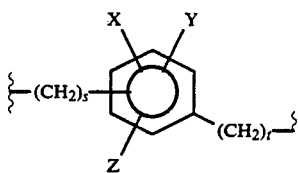

wherein s is 0 to 6 and t is 0 to 6,
(7)

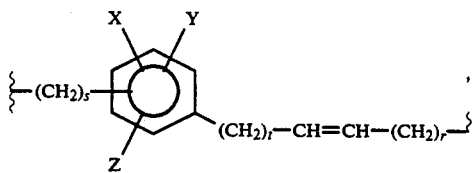

wherein r is 1 to 3 and s, and t are as defined above;
X, Y and Z are independently selected from the group consists of:
(a) hydrogen,
(b) C$_{1-10}$alkyl, unsubstituted or substituted with one or more substituents selected from:
 (i) aryl,
 (ii) substituted aryl in which the substituents are X', Y' and Z',
 (iii) heteroaryl,
 (iv) substituted heteroaryl in which the substituents are X', Y', and Z',
 (v) unsubstituted or substituted aryloxy, in which the substituents on aryl are X', Y' and Z',
 (vi) —OR$^9$,
 (vii) —OR$^{11}$,
 (viii) —OCOR$^9$,
 (ix) —OCO$_2$R$^9$,
 (x) —NR$^9$R$^{10}$,
 (xi) —CHO,
 (xii) —NR$^9$COC$_{1-6}$alkyl—R$^{10}$,
 (xiii) —NR$^9$CO$_2$C$_{1-6}$alkyl—R$^{10}$,
 (xiv) —NR$^9$CONR$^9$R$^{10}$,
 (xv) —OCONR$^9$R$^{10}$,
 (xvi) —CONR$^9$R$^{10}$,
(c) C$_{1-10}$alkyl wherein one or more of the alkyl carbons is replaced by a group selected from —NR$^9$—, —O—, —S(O)$_p$—, —CO$_2$—, —O$_2$C—, —CONR$^9$—, —NR$^9$CO—, —NR$^9$CONR$^{10}$—, —CO—, —CH(OH)—, alkenyl or alkynyl and the alkyl may be unsubstituted or substituted with one or more substituents selected from:
 (i) aryl,
 (ii) substituted aryl in which the substituents are X', Y' and Z',
 (iii) heteroaryl,
 (iv) substituted heteroaryl in which the substituents are X', Y', and Z',
 (v) unsubstituted or substituted aryloxy, in which the substituents on aryl are X', Y' and Z',
 (vi) —OR$^9$,
 (vii) —OR$^{11}$,
 (viii) —OCOR$^9$,
 (ix) —OCO$_2$R$^9$,
 (x) —NR$^9$R$^{10}$,
 (xi) —CHO
 (xii) —NR$^9$COC$_{1-6}$alkyl—R$^{10}$,
 (xiii) —NR$^9$CO$_2$C$_{1-6}$alkyl—R$^{10}$,
 (xiv) —NR$^9$CONR$^9$R$^{10}$,
 (xv) —OCONR$^9$R$^{10}$,
 (xvi) —CONR$^9$R$^{10}$,
(d) halogen,
(e) —NR$^9$R$^{10}$,
(f) —CN,
(g) —CHO,
(h) —CF$_3$,
(i) —SR$^{15}$, wherein R$^{15}$ is hydrogen C$_{1-6}$alkyl, trifluoromethyl, or phenyl,
(j) —SOR$^{15}$,
(k) —SO$_2$R$^{15}$,
(l) —CONR$^9$R$^{10}$,
(m) R$^{16}$O(CH$_2$)$_m$— wherein R$^{16}$ is hydrogen, C$_{1-6}$alkyl, hydroxy—C$_{2-3}$alkyl, —CF$_3$, phenyl, R$^{11}$ or naphthyl and m is 0, 1, 2, or 3,
(n) —CH(OR$^{17}$)(OR$^{18}$), wherein R$^{17}$ and R$^{18}$ are C$_{1-3}$alkyl or taken together form an ethyl or propyl bridge,
(o)

wherein R$^{16}$ and m are as defined above,
(p)

wherein R$^{16}$ and m are as defined above,
(q) —R$^{11}$;
or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;
X', Y' and Z' independently are selected from:
(a) hydrogen,
(b) C$_{1-7}$alkyl,
(c) C$_{2-6}$alkenyl,
(d) halogen,
(e) —(CH$_2$)$_m$—NR$^9$R$^{10}$, wherein R$^9$, R$^{10}$ and m are as defined above, (f) —CN,
(g) —CHO,
(h) —CF$_3$,
(i) —SR$^{15}$, wherein R$^{15}$ is as defined above,
(j) —SOR$^{15}$, wherein R$^{15}$ is as defined above,
(k) —SO$_2$R$^{15}$, wherein R$^{15}$ is as defined above,
(l) —CONR$^9$R$^{10}$, wherein R$^9$ and R$^{10}$ are as defined above,
(m) R$^{16}$O(CH$_2$)$_m$— wherein R$^{16}$ and m are as defined above,
(n) —CH(OR$^{17}$)(OR$^{18}$), wherein R$^{17}$ and R$^{18}$ are as defined above,
(o)

wherein R$^{16}$ and m are as defined above,
(p)

wherein R$^{16}$ and m are as defined above, and
(q) —R$^{11}$.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, R$^6$, R$^7$, R$^8$, R$^9$, R$^{10}$, R$^{11}$, X, Y, Z, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonly groups of specified number of carbon atoms, which are exemplified by formyl, acetyl, propanoyl, and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen" or "halo," as used herein, means fluoro, chloro, bromo and iodo.

The heteroaryl group as used herein includes acridine, carbazole, cinnoline, dibenzofuran, dibenzothiophene, quinoxaline, pyrrazole, indole, imidazole, benzotriazole, furan, benzofuran, quinoline, isoquinoline, pyrazine, pyridazine, pyridine, pyrimidine, pyrrole which are optionally substituted.

In the compound of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The aryl or aromatic group may include phenyl or naphthyl which are optionally substituted by from one- to three-members independently selected from the group consisting of X, Y and Z.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula NHR$^9$R$^{10}$).

One embodiment of the present invention encompasses the compound of Formula I wherein:
R$^1$ is selected from:

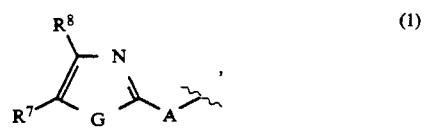

(1)

wherein G is N—R$^6$, O, or S,

(2)

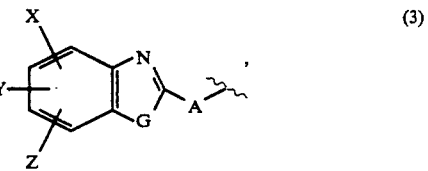

(3)

and

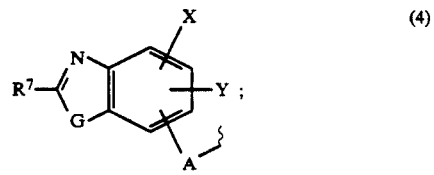

(4)

R$^2$ is independently selected from:
(1) hydrogen;

(2) phenyl;
(3) substituted phenyl in which the substituents are X, Y and Z;
(4) $C_{1-10}$alkyl;
(5) substituted $C_{1-10}$alkyl in which one or more substituent(s) is(are) selected from:
 (a) hydroxy,
 (b) $C_{1-6}$alkoxy,
 (c) phenyl—$C_{1-3}$alkoxy,
 (d) substituted phenyl—$C_{1-3}$alkoxy, in which the substituents on phenyl are X, Y and Z,
 (e) —OCO—$C_{1-6}$alkyl,
 (f) —COOR$^{20}$, wherein R$^{20}$ is hydrogen or $C_{1-6}$alkyl,
 (g) —CHO,
 (h) phenyl, and
 (i) substituted phenyl in which the substituents are X, Y and Z;
(6) $C_{3-10}$alkenyl;
(7) substituted $C_{3-10}$alkenyl in which one or more substituents(s) is(are) selected from:
 (a) hydroxy,
 (b) $C_{1-6}$alkoxy,
 (c) phenyl—$C_{1-3}$alkoxy,
 (d) substituted phenyl—$C_{1-3}$alkoxy, in which the substituents on phenyl are X, Y and Z,
 (e) —OCO—$C_{1-6}$alkyl,
 (f) —COOR$^{20}$, wherein R$^{20}$ is as defined above,
 (g) —CHO,
 (h) phenyl, and
 (i) substituted phenyl in which the substituents are X, Y and Z;
(8) $C_{3-10}$alkenyl;
(9) substituted $C_{3-10}$alkenyl in which one or more substituents(s) is(are) selected from:
 (a) hydroxy,
 (b) $C_{1-6}$alkoxy,
 (c) phenyl—$C_{1-3}$alkoxy,
 (d) substituted phenyl—$C_{1-3}$alkoxy, in which the substituents on phenyl are X, Y and Z,
 (e) —OCO—$C_{1-6}$alkyl,
 (f) —COOR$^{20}$, wherein R$^{20}$ is as defined above,
 (g) —CHO,
 (h) phenyl,
 (i) substituted phenyl in which the substituents are X, Y and Z; and
(10) —R$^{11}$;

R$^6$ is selected from the group of:
(1) hydrogen,
(2) $C_{1-6}$alkyl, unsubstituted or substituted with:
 (a) hydroxy,
 (b) $C_{1-6}$alkoxy,
 (c) phenyl, unsubstituted or substituted with X, Y and Z,
 (d) —OR$^{11}$,
(3) $C_{3-6}$alkenyl, unsubstituted or substituted with:
 (a) hydroxy,
 (b) phenyl, unsubstituted or substituted with X, Y and Z, or
 (c) $C_{1-6}$alkoxy, and
(4) phenyl, unsubstituted or substituted with X, Y and Z,
(5) —R$^{11}$,
(6) X, Y or Z;

R$^7$ and R$^8$ independently are selected from the group consisting of:
(1) hydrogen,
(2) $C_{1-7}$alkyl,
(3) $C_{2-6}$alkenyl,
(4) —CF$_3$,
(5) R$^{14}$O(CH$_2$)$_m$— wherein R$^{14}$ is hydrogen, $C_{1-6}$alkyl, hydroxy-$C_{2-3}$alkyl, —CF$_3$, phenyl, R$^{11}$ or naphthyl and m is 0, 1, 2 or 3,

wherein R$^{14}$ and m are as defined above;
(7) phenyl-(CH$_2$)$_m$— wherein m is as defined above and the phenyl is unsubstituted or substituted with X, Y and Z,
(8) heteroaryl-(CH$_2$)$_m$—wherein m is as defined above and the heteroaryl is unsubstituted or substituted with X, Y and Z,
(9) —CH=CH—phenyl wherein the phenyl is unsubstituted or substituted with X, Y and Z;

R$^{11}$ is selected from:
 (a) —PO(OH)O$^-$M$^+$, wherein M$^+$ is a positively charged inorganic or organic counterion,
 (b) —SO$_3^-$M$^+$,
 (c) —CO(CH$_2$)$_q$CO$_2^-$M$^+$, wherein q is 1 to 3, and
 (d) —CO—$C_{1-6}$alkyl—NR$^{20}$R$^{21}$, wherein R$^{20}$ is as defined above and R$^{21}$ is selected from the definitions of R$^{20}$;

A is selected from the group consisting of:
(1) a bond,
(2) $C_{1-10}$alkyl, and
(3)

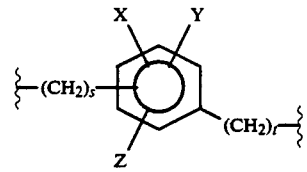

wherein s is 0 to 2 and t is 0 to 2;

X, Y and Z are independently selected from the group consisting of:
 (a) hydrogen,
 (b) $C_{1-7}$alkyl,
 (c) $C_{2-6}$alkenyl,
 (d) halogen,
 (e) —(CH$_2$)$_m$—NR$^{20}$R$^{21}$, wherein R$^{20}$, R$^{21}$ and m are as defined above,
 (f) —(CH$_2$)$_m$—CONR$^{20}$R$^{21}$, wherein R$^{20}$, R$^{21}$ and m are as defined above,
 (g) —(CH$_2$)$_m$—NR$^{20}$—COR$^{14}$, wherein R$^{14}$, R$^{20}$ and m are as defined above.
 (h) —O—(CH$_2$)$_m$—CONR$^{20}$R$^{21}$, wherein R$^{20}$, R$^{21}$ and m are as defined above,
 (i) —CN,
 (j) —CHO,
 (k) —CF$_3$,
 (l) R$^{14}$O(CH$_2$)$_m$—wherein R$^{14}$ and m is as defined above,
 (m) —R$^{11}$.

Another embodiment of the present invention encompasses the compounds of Formula I wherein:
R$^1$ is

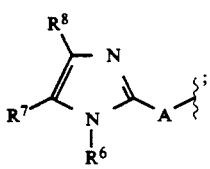

$R^2$ is hydrogen or methyl;
$R^6$ is hydrogen, methyl, benzyl, 3-fluorobenzyl, $R^{11}$ or —$C_{1-4}$alkyl—$OR^{11}$;
$R^7$ and $R^8$ are independently selected from: hydrogen, methyl, $CH_3OCH_2$—, $HOCH_2$—, phenyl, 3,5-difluorophenyl, 3-fluorophenyl, 3,4-difluorophenyl, 3,5-dichlorophenyl, 3-methoxyphenyl, 3-trifluoromethylphenyl, 3-hydroxyphenyl, 4-hydroxyphenyl, 3,5-dihydroxyphenyl, 4-tert-butylphenyl, 3,4-methylenedioxyphenyl, 3,5-trifluoromethylphenyl, 4-methoxyphenyl, 3,5-dimethoxyphenyl, 3-trifluoromethoxyphenyl, 3,5-di(trifluoromethoxy)phenyl, 2-methoxyphenyl, 3-isopropyloxyphenyl, 3-ethoxyphenyl, 3,5-diethoxyphenyl, 3,4,5-trimethoxyphenyl, 3-hydroxyethyloxyphenyl, 3-propyloxyphenyl, 3-isobutyloxyphenyl, 3-methylphenyl, 3,5-dimethylphenyl, 3-ethylphenyl, 3,5-diethylphenyl, and phenylethyl;
A is —$CH_2$—, phenyl, or benzyl;
and pharmaceutically acceptable salts thereof.

Specific compounds of the present invention include the compounds identified as follows: 42-(4'-phenyl-2'-imidazolylmethyloxy)-rapamycin.

B. Preparation of Compounds Within the Scope of the Present Invention

A starting material for the preparation of the compounds of this invention is rapamycin:

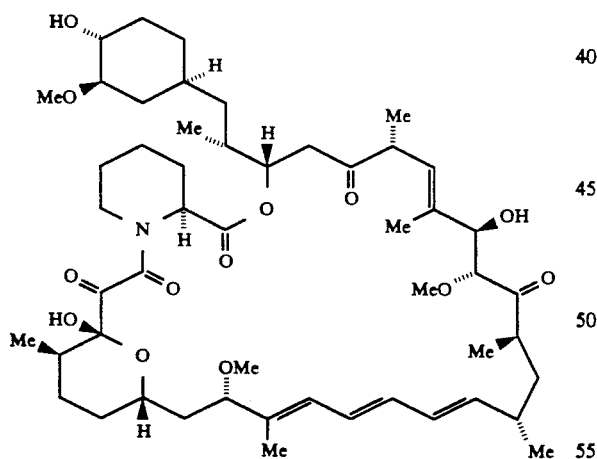

The production and characterization of rapamycin is well known in the literature (see U.S. Pat. No. 3,929,992 issued Dec. 30, 1975; U.S. Pat. No. 3,993,749 issued Nov. 23, 1976). Analogs of rapamycin, such as 30-desmethylrapamycin (see PCT Patent Publication WO 92/14737 or 29-hydroxy rapamycin (See U.S. Pat. No. 5,138,051) may also be employed as starting material to give analagous derivatives.

The novel processes for preparing the novel compounds of the present invention are illustrated as follows, wherein $R^1$ and $R^2$ are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

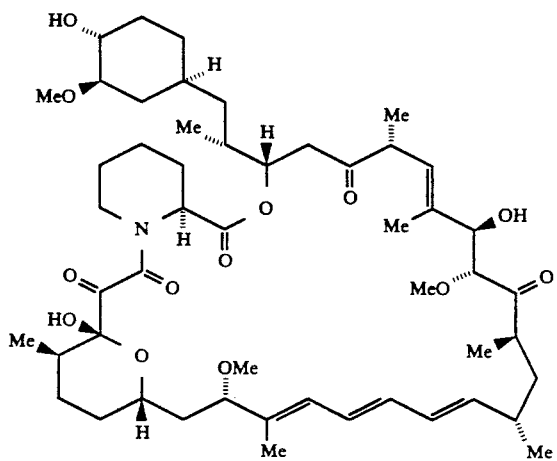

1) TBDMS triflate
   lutidine
   $CH_2Cl_2$ 2) 10% TsOH
   MeOH
   $CH_3CN$

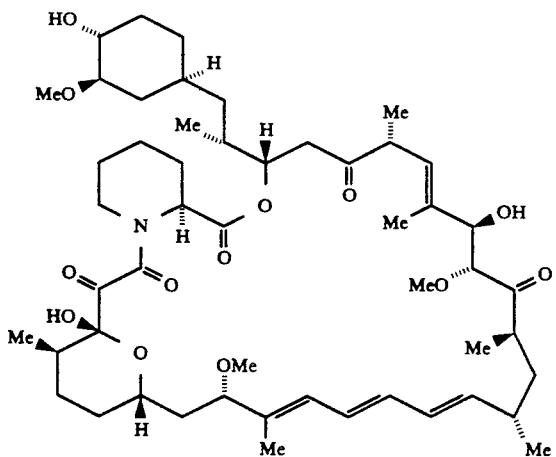

REACTION SCHEME B
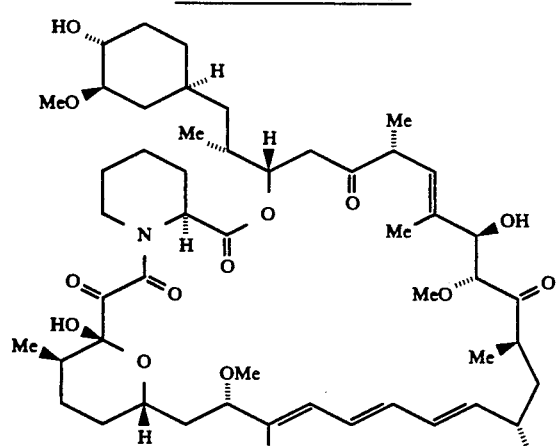
(R¹)₃Bi(OAc)₂
Cu(OAc)₂
CH₂Cl₂
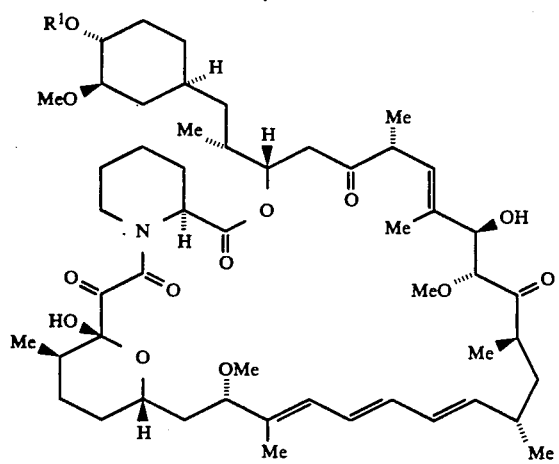
REACTION SCHEME C
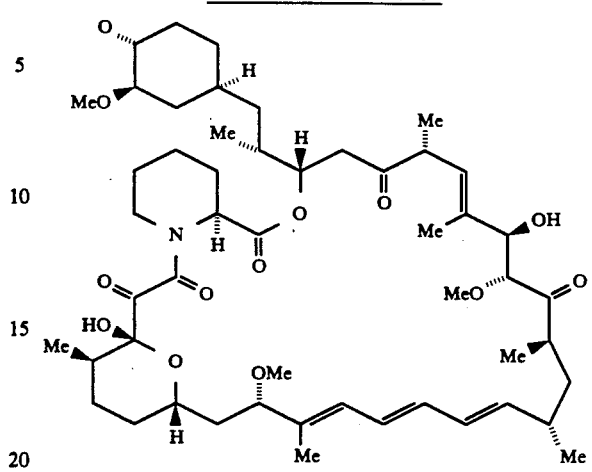
$$R^1O\underset{NH}{\overset{}{\diagdown}}CCl_3$$
CF₃SO₃H(cat.)
cyclohexane/
CH₂Cl₂
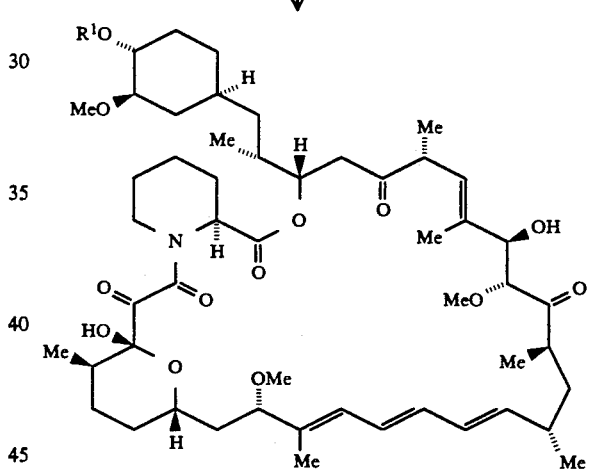
REACTION SCHEME E
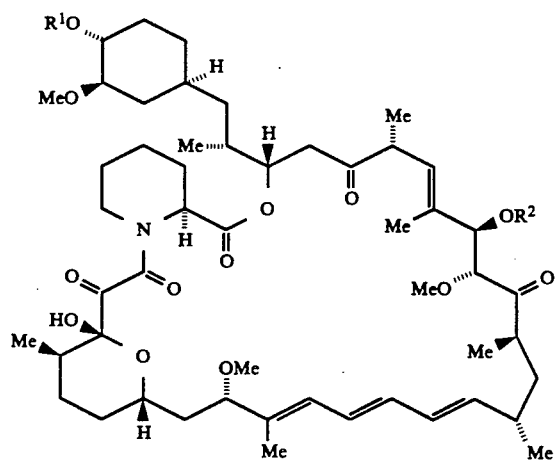

-continued
REACTION SCHEME E
1) OsO₄
   pyridine
   Et₂O
2) NaIO₄
   THF/H₂O
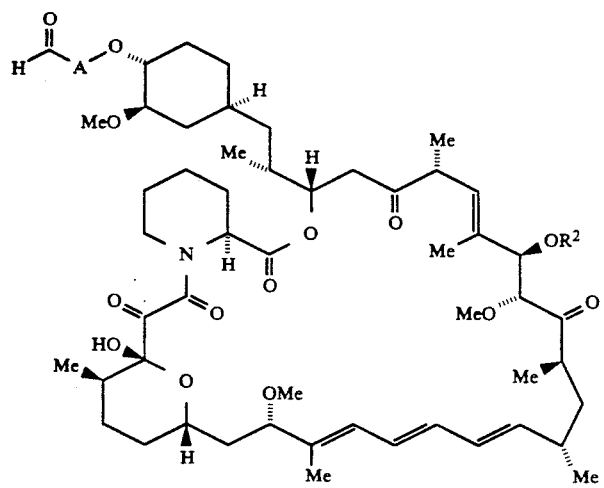
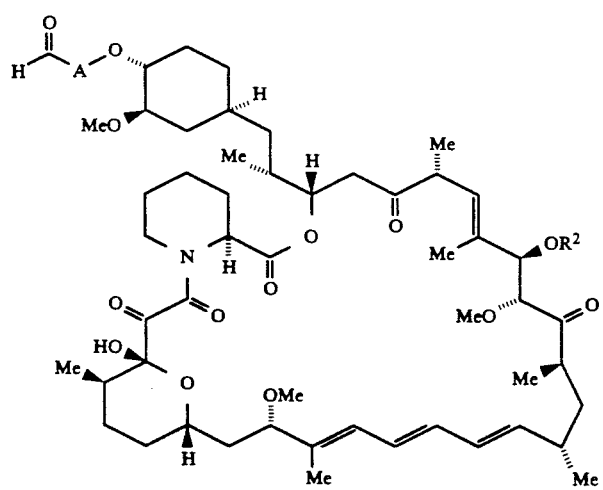
NaClO₂
NaH₂PO₄(aq.)
2-methyl-2-
butene
t-BuOH

REACTION SCHEME E
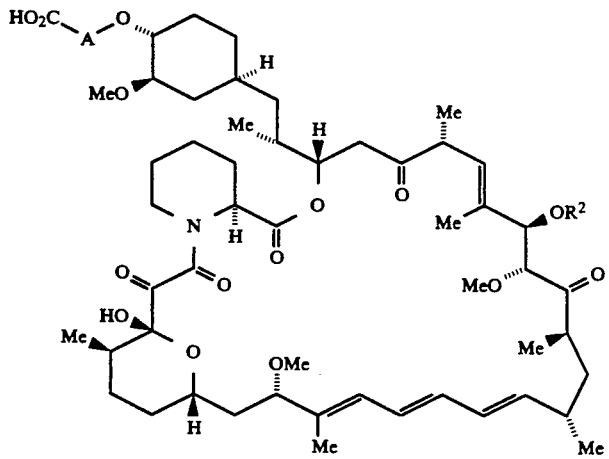
REACTION SCHEME F
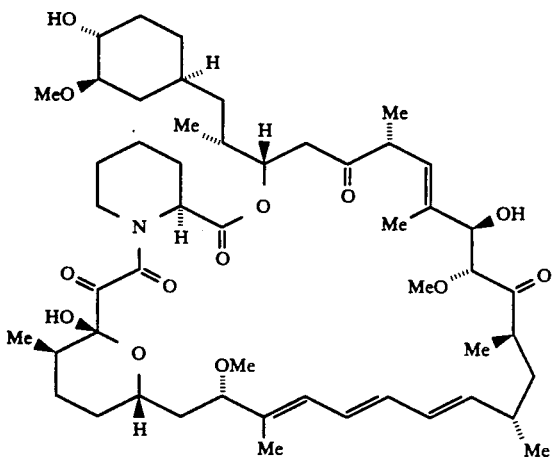
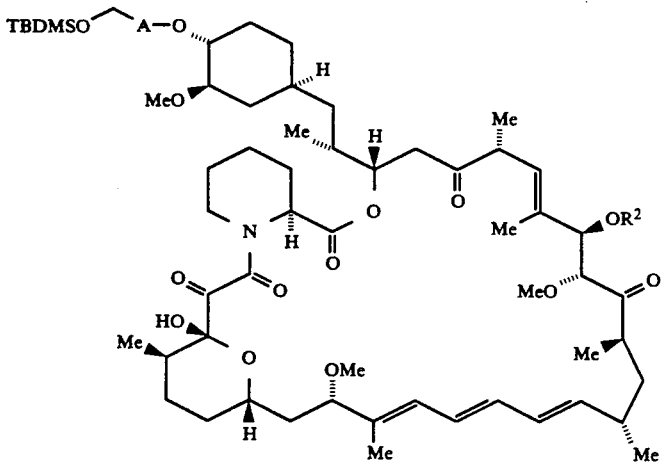

REACTION SCHEME F
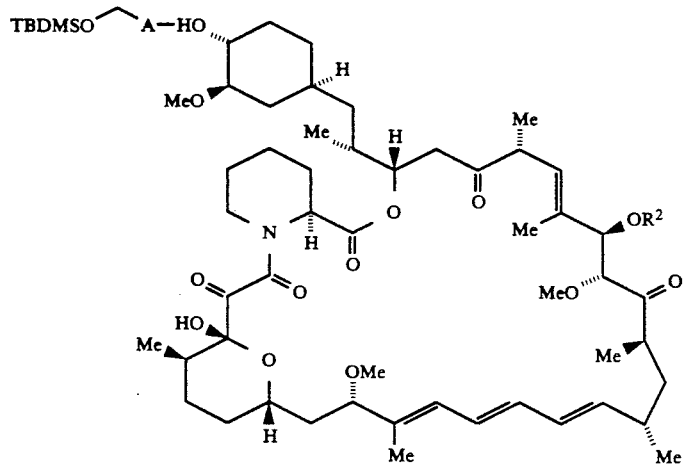
1) 10% Ts OH
   MeOH
   CH₂Cl₂
2) Dess-Martin          or
   oxidation            TPAP(cat.)
   CH₂Cl₂               NMO
                        4a sieves
                        CH₂Cl₂
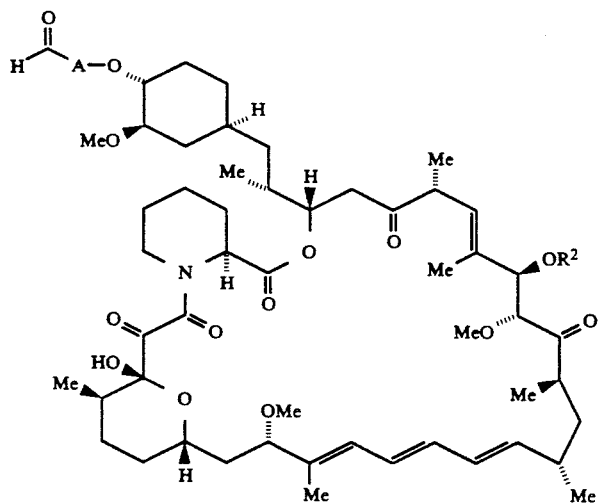

REACTION SCHEME G
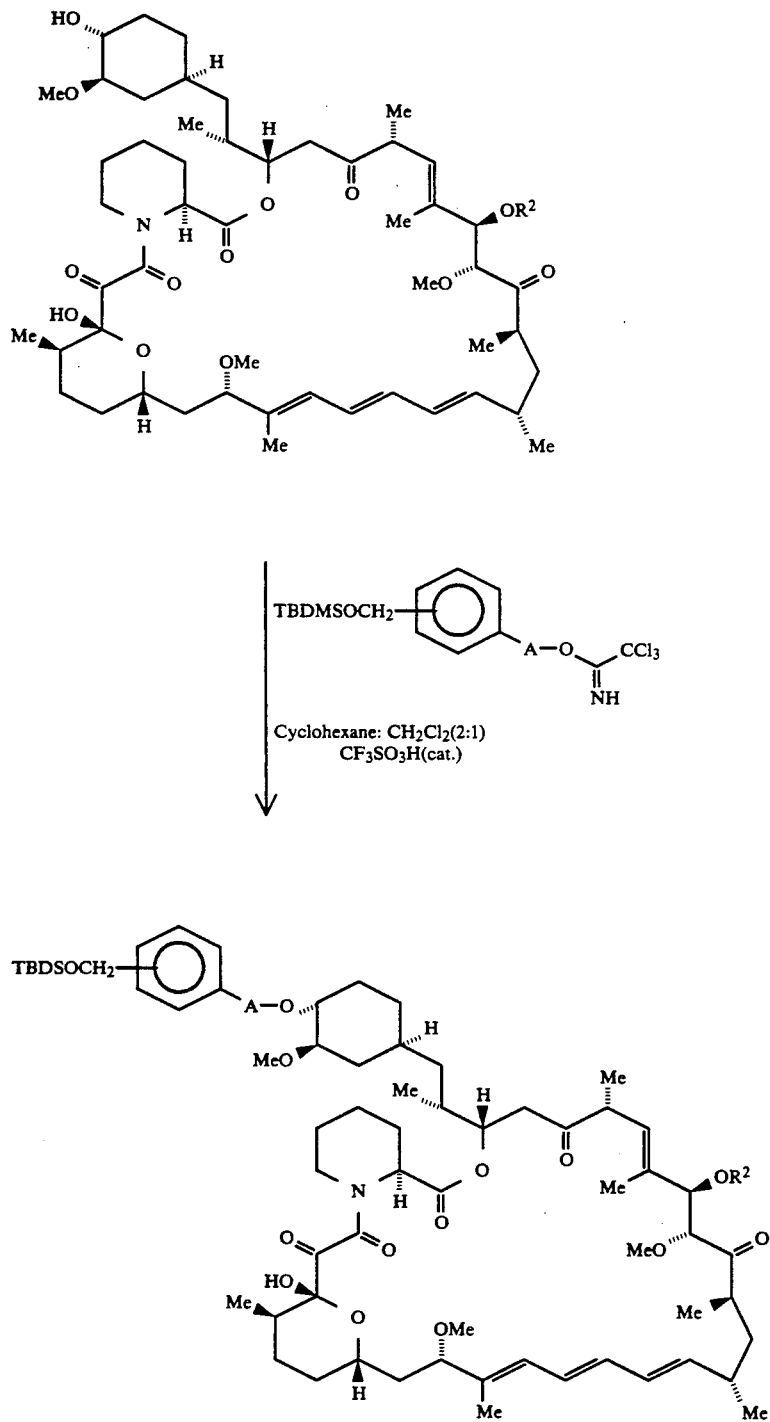

REACTION SCHEME H
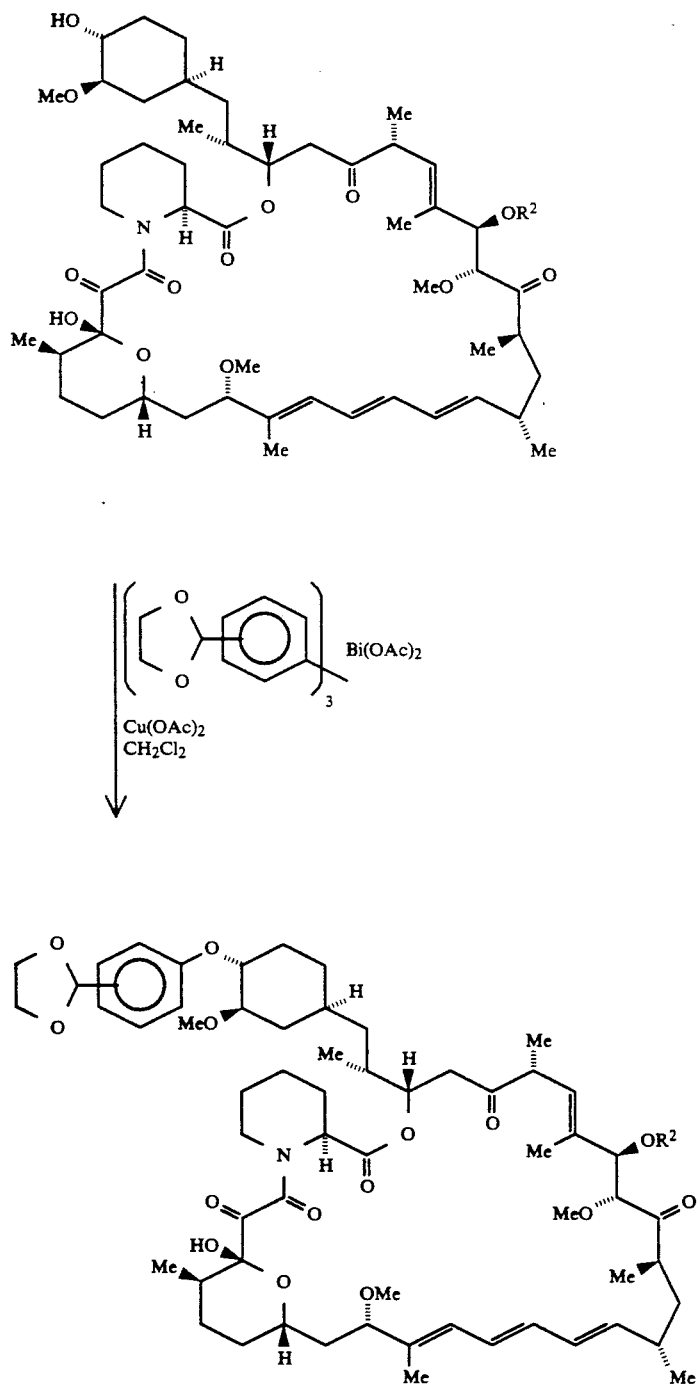

REACTION SCHEME I
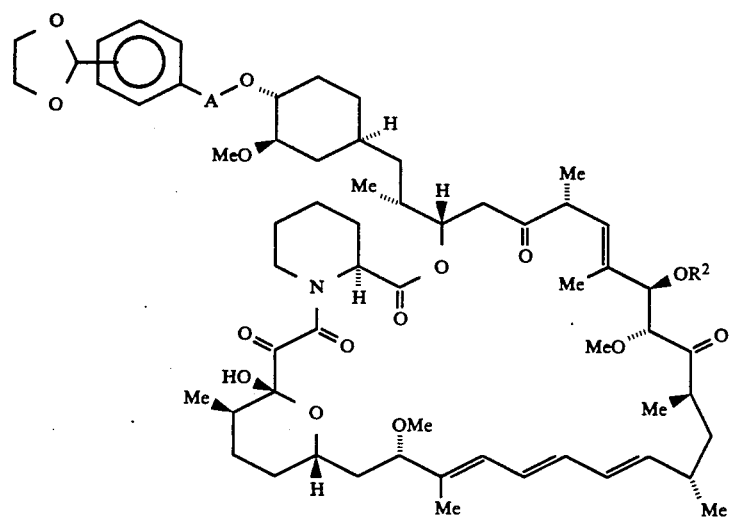
↓ 10% TsOH
MeOH
CH₂Cl₂
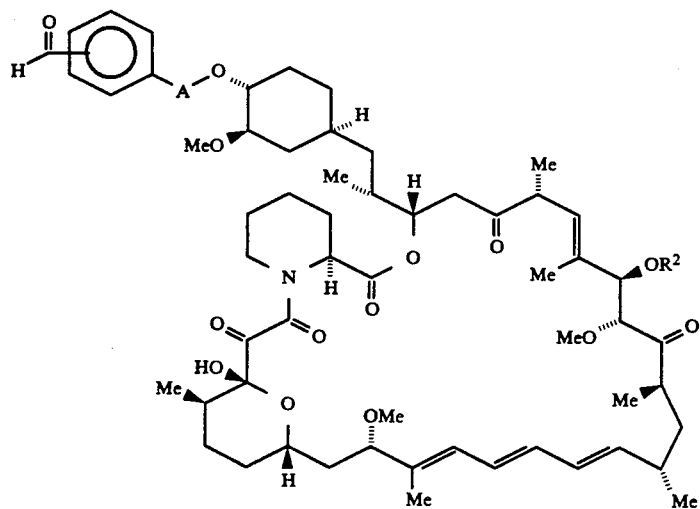

REACTION SCHEME J
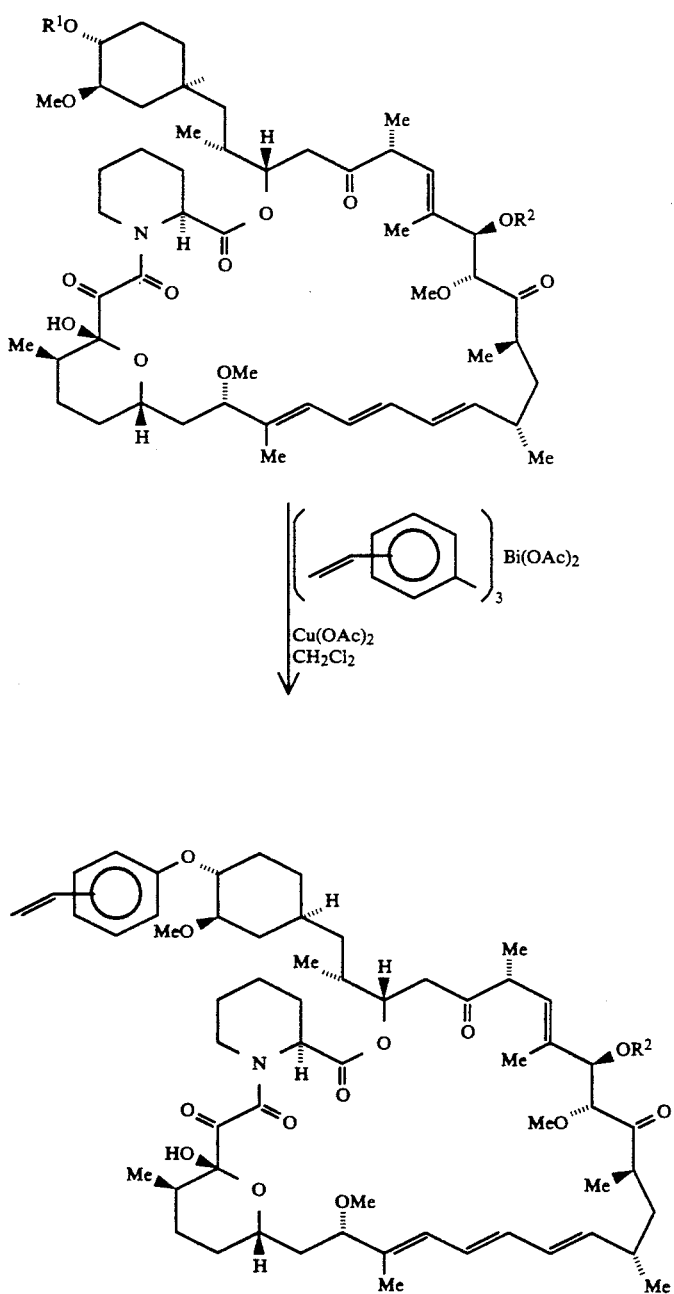

REACTION SCHEME L
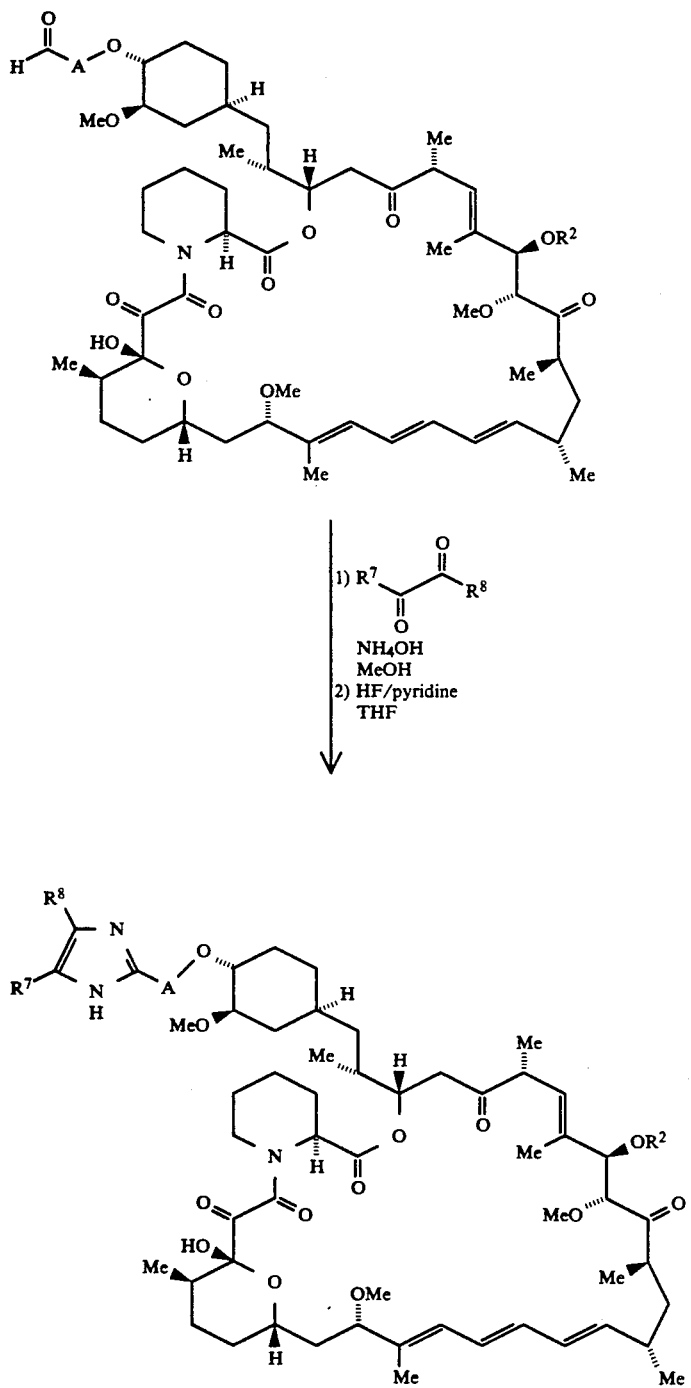

REACTION SCHEME M
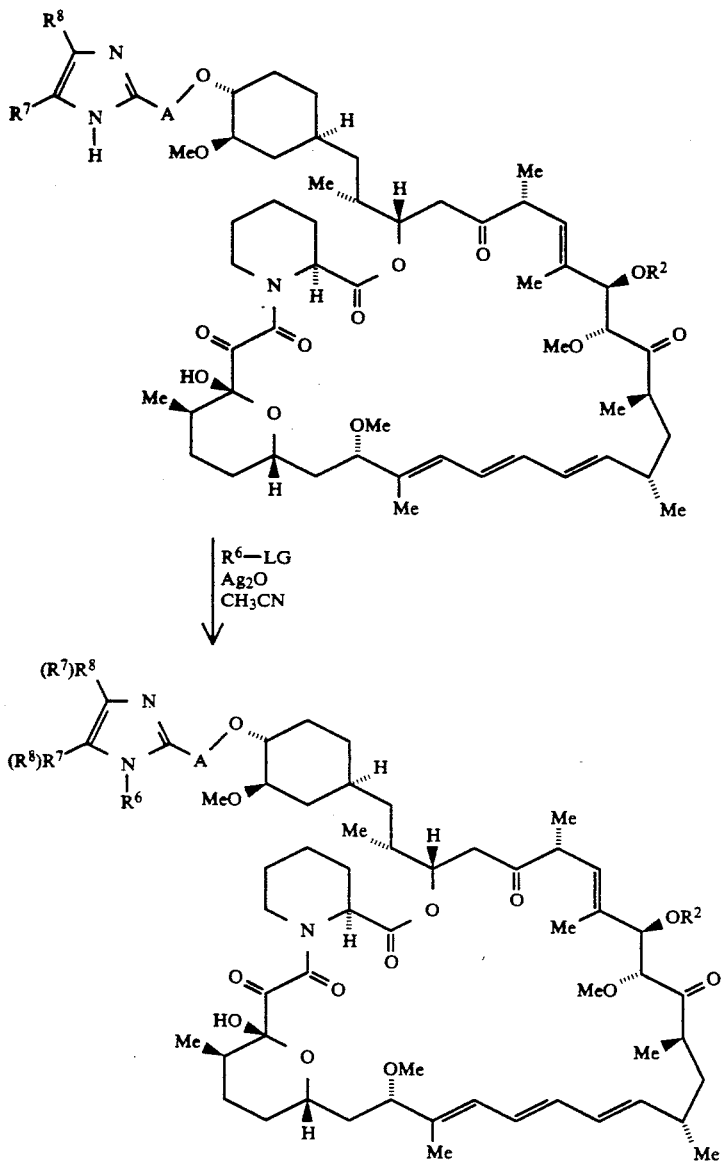
REACTION SCHEME N
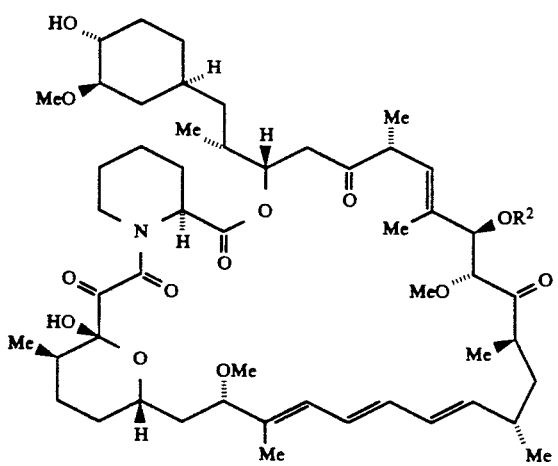

5,310,903
35                                                                  36
-continued
REACTION SCHEME N
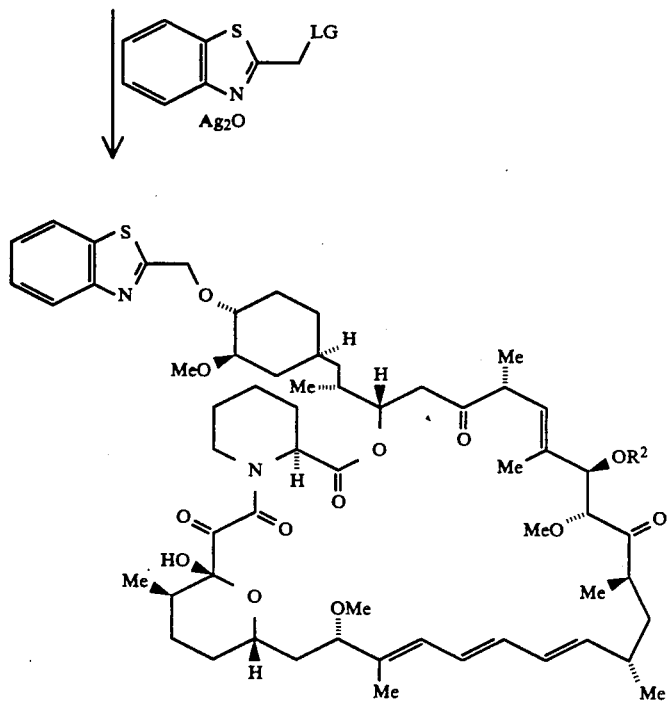
REACTION SCHEME O
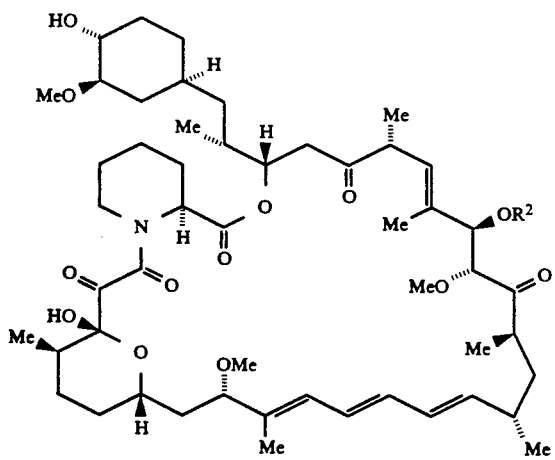
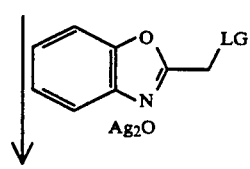

REACTION SCHEME O
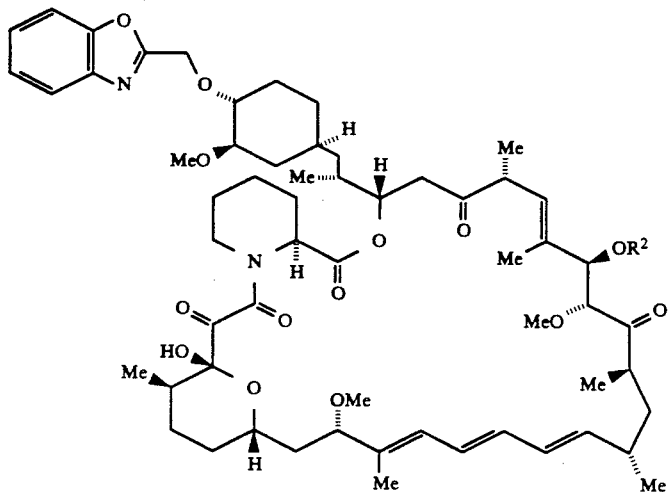
REACTION SCHEME P
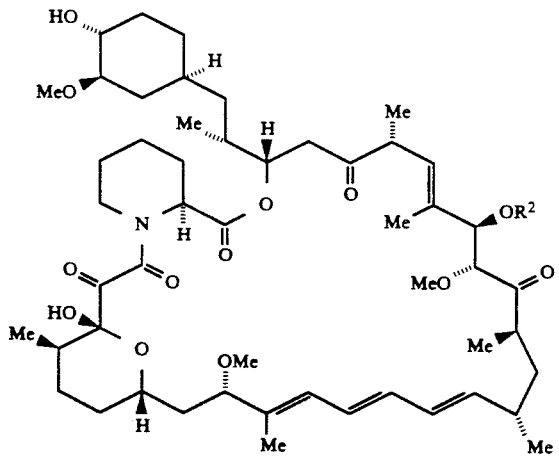
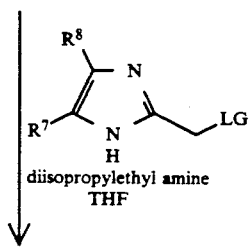
diisopropylethyl amine
THF

REACTION SCHEME P

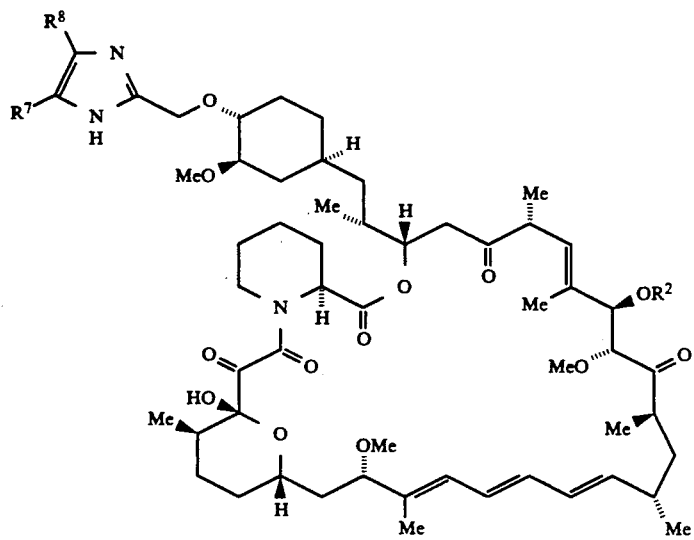

REACTION SCHEME Q

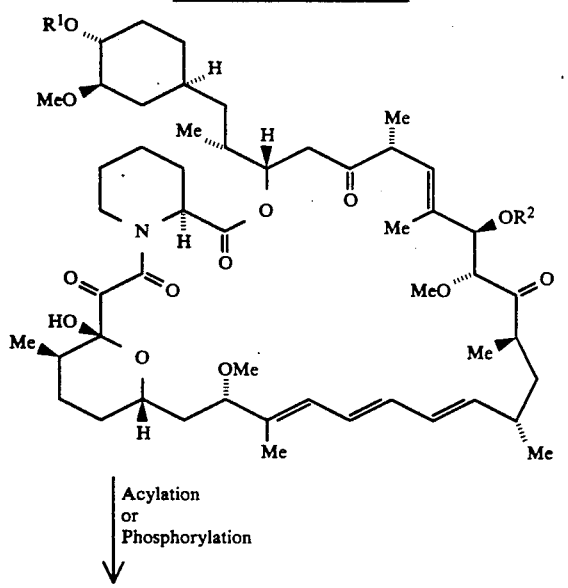

Acylation
or
Phosphorylation

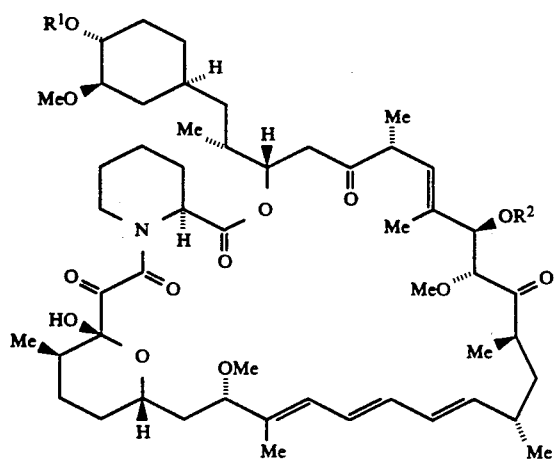

Reaction Scheme A

Protection of the C-31 and/or the C-42 hydroxy group may be accomplished by methods known in the prior art for rapamycin (see e.g. U.S. Pat. No. 5,120,842) such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like. For example, as shown in Reaction Scheme A, rapamycin may be protected at C-42 as the t-butyldimethylsilyl ether by treatment with one equivalent of t-butyldimethylsilyl trifluoromethanesulfonate in methylene chloride to give the C-42-di-O-TBDMS macrolide. Treatment with two equivalents of TBDMS triflate followed by treatment with acetic acid or toluene-sulfonic acid in methanol results in selective removal of the C-42 ether to give the C-31-O-TBDMS macrolide.

Reaction Scheme B

As shown in Reaction Scheme B, a solution of rapamycin in an inert organic solvent such as methylene chloride, benzene, toluene, chloroform, or the like or mixtures thereof may be treated with a triarylbismuth diacetate reagent (wherein $R^1$ is aryl) (prepared immediately prior to use by the addition of acetic acid to a suspension of a triarylbismuth carbonate in an inert organic solvent such as methylene chloride, chloroform or the like or mixtures thereof) in the presence of a catalytic amount of copper(II) acetate at a temperature of 20°–50° C., preferably room temperature, for a period of one hour to seven days, preferably one day, to give the 42-O-aryl rapamycin and/or the 31, 42-di-O-aryll rapamycin. Alternatively, the triarylbismuth(V) reagent may be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent may be used without purification or may be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D.H.E., et al., *J. Chem. Soc. Chem. Commun.*, 1986, 65 and references cited therein.

Similarly, the 31-O-aryl compounds may be prepared by protecting the 42-alcohol of rapamycin with a protecting group, such as with a tert-butyl dimethylsilyl group, followed by arylation of the 31-position with a triaryl bismuth reagent. Removal of the protecting group provides the 31-O-aryl compounds. In the case of the tert-butyl dimethylsilyl protecting group, deprotection can be accomplished under mildly acidic conditions.

If desired, the 31-hydroxy-42-O-aryl rapamycin, or 31-O-aryl-42-hydroxy rapamycin may be treated with a different triarylbismuth diacetate reagent (prepared immediately prior to use by procedures analogous to those disclosed above), to give mixed 31-O-aryl-42-O-aryl macrolides.

Reaction Scheme C

As shown in Reaction Scheme C, a solution of the rapamycin in an inert organic solvent such as methylene chloride, chloroform, pentane, hexane, cyclohexane, heptane or the like or mixtures thereof is treated with an alkyl, alkenyl or alkynyl trichloroacetimidate reagent (prepared by the reaction of an appropriate sodium alkoxide with trichloroacteonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methane-sulfonic acid, benzenesulfonic acid, p-nitrobenzene-sulfonic acid, p-bromobenzenesulfonic acid, p-chlorobenzenesulfonic acid, or p-methoxybenzenesulfonic acid, or mixtures thereof at a temperature of 20°-50° C., preferably room temperature, for a period of one hour to seven days, preferably one day, to give the 31- and/or 42-O-alkyl, -alkenyl or -alkynyl rapamycin derivative.

In addition, the procedure of Reaction Schemes A, B, and C may be combined to produce rapamycin derivatives bearing O-aryl, O-alkyl, O-alkenyl and/or O-alkynyl substituents at the 31 and 42 positions.

The procedures described in Reaction Scheme B may be conducted on the mono-substituted products of Reaction Scheme C (and visa versa) to obtain the mixed disubstituted compounds. In fact, within Reaction Schemes B and C, treatment of the mono-substituted product with a different reagent will afford the mixed disubstituted compounds.

Reaction Scheme E

As shown in Reaction Scheme E, the 42-hydroxy-31-$R^2$O-macrolide or alternatively the 31-hydroxy-42-$R^1$O-macrolide (not depicted) (wherein $R^3$ is protected hydroxy or hydrogen) may be reacted with an alkenyl trichloroacetimidate (wherein $R^1$ is $C_{3-10}$ alkenyl) under conditions described in Reaction Scheme C to give the C-42-O-alkenyl macrolide. Treatment with a stoichiometric amount of osmium tetraoxide in an inert organic solvent, such as diethyl ether or tetrahydrofuran, in the presence of an amine base, such as pyridine or 4-methylmorpholine N-oxide, at or near room temperature gives the corresponding glycol. Treatment of the glycol with sodium metaperiodate in a solution of tetrahydrofuran/water gives the aldehyde (wherein A is $C_{1-8}$ alkyl). Alternatively, the alkenyl macrolide may be treated with sodium metaperiodate in the presence of a catalytic amount of osmium tetraoxide in an organic solvent to give the aldehyde directly. The aldehyde may be further oxidized to the carboxylic acid by treatment with sodium chlorite in buffered, aqueous tert-butanol.

Reaction Scheme F

A solution of the 31,42-dihydroxy macrolide (or the 31- or 42-mono-substituted hydroxy macrolide) in an inert organic solvent such as methylene chloride, chloroform, pentane, hexane, cyclohexane, heptane or the like or mixtures thereof is treated with a protected-hydroxy substituted-alkenyl or alkynyl trichloroacetimidate (wherein A is as defined above and contains an allylic group or a benzylic group adjacent to the oxygen) (prepared by the reaction of an appropriate sodium alkoxide with trichloroacetonitrile, such as described by Wessel, H.P., Iversen, T., Bundle, D.R., *J. Chem. Soc., Perkin Trans. I*, 1985, 2247) in the presence of a mold acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxy-benzenesulfonic acid, or mixtures thereof at a temperature of 20°-50° C., preferably 40° C., for a period of one hour to seven days, preferably 6 hours, to give a mixture of the protected hydroxy substituted 31-O-alkenyl or -alkynyl 42-hydroxy macrolide, the 31-hydroxy 42-O-alkenyl or -alkynyl macrolide and the 31,42-di-O-alkenyl or -alkynyl macrolide.

As further shown in Reaction Scheme F the silyl protecting group is removed such as by treatment with toluenesulfonic acid in a mixture of methanol and methylene chloride and the resultant primary hydroxyl group is converted to the aldehyde by Dess-Martin oxidation or preferably by treatment with tetra-n-propylammonium perruthenate (TPAP) and 4-methyl-morpholine-N-oxide (NMO).

Reaction Scheme G

The appropriate 31,42-dihydroxy macrolide (or the 31- or 42-mono-substituted hydroxy macrolide) is treated with a protected benzyloxy-substituted alkenyl or alkynyl trichloroacetimidate (wherein A is as defined above and contains an allylic group adjacent to the oxygen) under conditions essentially as described in Reaction Scheme F to give the macrolide bearing a pendent protected benzyloxy group.

Reaction Scheme H

A solution of the 31,42-dihydroxy macrolide (or the 31- or 42-mono-substituted hydroxy macrolide) in an inert organic solvent such as methylene chloride, benzene, toluene, chloroform, or the like or mixtures thereof is treated with a triarylbismuth diacetate reagent (wherein aryl is protected benzaldehyde, benzyloxy, benzimidazole, benzothiazole, or benzoxazole) (prepared immediately prior to use by the addition of acetic acid to a suspension of a triarylbismuth carbonate in an inert organic solvent such as methylene chloride, choroform or the like or mixture thereof) in the presence of a catalytic amount of copper(II) acetate at a temperature of 20°-50° C., preferably room temperature, for a period of one hour to seven days, preferably one day, to give the 31-and/or 42-O-aryl- macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D.H.E., et al., *J. Chem. Soc. Chem. Commun.*, 1986, 65 and references cited therein.

Reaction Scheme

The acetal protecting group is removed from the macrolide (wherein A is as defined above) by treatment with toluenesulfonic acid in methanol to provide the corresponding benzaldehyde.

Reaction Scheme

A solution of the 31,42-dihydroxy macrolide (or the 31- or 42-mono-substituted hydroxy macrolide) in an inert organic solvent such as methylene chloride, benzene, toluene, chloroform, or the like or mixtures thereof is treated with an alkenyl triarylbismuth diacetate reagent (prepared immediately prior to use by the addition of acetic acid to a suspension of a triarylbismuth carbonate in an inert organic solvent such as methylene chloride, chloroform, or the like or mixtures thereof) in the presence of a catalytic amount of copper-(II) acetate at a temperature of 20°-50° C., preferably 40° C., for a period of one hour to seven days, preferably 6 hours, to give a mixture of the 31-O-styrene-42-hydroxy macrolide, the 31-hydroxy-42-O-styrene macrolide, and the 31,42-di-O-styrene macrolide.

Reaction Scheme L

A variety of imidazoles may be prepared from the corresponding aldehyde. The aldehyde may be reacted with glyoxal, an α-keto aldehyde or an α,β-diketone (where in $R^7$ and $R^8$ are as defined above) in an alcoholic solvent, such as methanol, in the presence of ammonium hydroxide to give the corresponding imidazolyl macrolide. Treatment with hydrogen fluoride/pyridine removes any silyl protecting groups that may be present.

Reaction Scheme M

The free nitrogen of the imidazole substituent may be alkylated at either nitrogen atom of the imidazole by treatment with an appropriate alkyl, alkenyl or arylalkyl halide (wherein LG is I, Br or Cl) in the presence of silver (I) oxide to give the desired N-substituted imidazolyl macrolide.

The imidazole may be further modified by utilizing the methods of Reaction Scheme B. It is noted that such procedures may also be performed on dihydroxyl imidazoles to give the disubstituted imidazole macrolides, and by employing appropriate protecting groups to give the mixed disubstituted imidazoles. The procedures described in Reaction Scheme L-N are readily applicable to the preparation of compounds bearing analagous functionality at C-31.

Reaction Scheme N

Benzothiazole compounds can be prepared by treatment of the suitably protected macrolide with a benzothiazole containing a leaving group (LG=halogen or OTf) with a suitable base such as silver (I) oxide.

Reaction Scheme O

Benzoxazole compounds can be prepared by treatment of the suitably protected macrolide with a benzothiazole containing a leaving group (LG=halogen or OTf) with a suitable base such as silver (I) oxide. Such compounds may be modified essentially as described in Reaction Scheme M.

Reaction Scheme P

Imidazolidyl ether containing compounds can be prepared by treatment of the suitable protected macrolide with an imidazolidyl reagent bearing a leaving group such as p-toluenesulfonate, p-nitrobenzenesulfonate, methanesulfonate, acetate, trifluoroacetate, benzoate, p-nitrobenzoate, and the like in an inert solvent such as tetrahydrofuran, diethyl ether, methylene chloride, benzene, acetonitrile with an amine base such as triethyl amine, diisopropylethyl amine, pyridine, 2,6-dimethylpyridine and the like at or about room temperature. Such compounds may be modified essentially as described in Reaction Scheme M.

Reaction Scheme Q

Hydroxy macrolides (wherein $R^1$ and/or $R^2$ bear a hydroxy group) may be further derivatized by alkylation, acylation or phosphorylation to give ether, ester or phosphate derivatives (wherein $R^1$ and/or $R^2$ bear an —$OR^{11}$ as defined above) by procedures well known to the practitioner of the art.

The object compounds of Formula I obtained according to the reactions as explained above can be isolated and purified in a conventional manner, for example, extraction, precipitation, fractional crystallization, recrystallization, chromatography, and the like.

In the compounds of Formula I $R^1O—$ may be substituted at C-31 or C-42 or both C-31 and C-42, but it is preferred that $R^1O—$ is substituted at C-42.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, as diastereomeric mixtures and as individual diastereomers, with all isomeric forms of the compounds being included in the present invention.

The compounds of the present invention are capable of forming salts with various inorganic and organic acids and bases and such salts are also within the scope of this invention. Examples of such acid addition salts (which are negative counterions defined herein as M−) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as M+) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl, diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of the existing salt for another anion on a suitable ion exchange resin.

C. Utility of the compounds within the scope of the invention

The compounds of Formula I may be employed as immunosuppressants or antimicrobial compounds by methods and in dosages known in the prior art for rapamycin. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms, particularly fungal infections.

The compounds of Formula I are also useful for treating or preventing inflammatory and hyperproliferative skin diseases and cutaneous manifestations of immunologically-mediated illnesses such as: psoriasis, atopical dermatitiis, contact dermatitis and further eczematous dermatitises, seborhoeic dermatitis, Lichen planus, Pemphigus, bullous Pemphigoid, Epidermolysis bullosa, urticaria, angioedemas, vasculitides, erythemas, acne, cutaneous eosinophilias or Alopecia areata. More particularly, the compounds of Formula I are useful in hair revitalizing, such as in the treatment or prevention of male pattern alopecia or alopecia senilis, by providing epilation prevention, hair germination, and/or a promotion of hair generation and hair growth.

The compounds of Formula I are further useful for treating or preventing reversible obstructive airways disease, including conditions such as asthma, including bronchial asthma, allergic asthma, intrinsic asthma, extrinsic asthma and dust asthma, particularly chronic or inveterate asthma (for example late asthma and airway hyper-responsiveness), bronchitis and the like. The compounds of Formula I may also be useful for treating hepatic injury associated with ischemia.

The compounds of Formula I are also useful for treating multidrug resistance of tumor cells, (i.e. enhancing the activity and/or sensitivity of chemotherapeutic agents), preventing or treating inflammation of mucosa or blood vessels, $LTB_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis, or intestinal lesions associated with thermal burns, cytomegalovirus infection, particularly HCMV infection, idiopathic thrombocytopenic purpura and Basedow's disease.

Further, the compounds of Formula I are also useful for treating or preventing renal diseases selected from interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases selected from hyperthyroidism; hematic diseases selected from pure red cell aplasia, aplastic anemia, hypoplastic anemia, autoimmune hemolytic anemia, agranulocytosis and anerythroplasia, bone diseases such as osteoporosis; respiratory diseases selected from sarcoidosis, fibroid lung and idiopathic interstitial pneumonia; eye diseases selected from herpetic keratitis, conical cornea, dystrophia epithelialis corneae, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitis syndrome, polyarteritis nodosa and myocardosis; collagen diseases selected from scleroderma, Wegener's granuloma and Sjogren's syndrome, adiposis; eosinophilic fasciitis; periodontal disease; and muscular dystrophy.

The compounds of Formula I are useful for the treatment of fungal infections in animals, especially mammals, including humans, in particular humans and domesticated animals (including farm animals). The compounds may be used for the treatment of topical fungal infections in man caused by, among other organisms, species of Candida, Trichophyton, Microsporum or Epidermophyton or in mucosal infections caused by *Candida albicans* (e.g. thrush and vaginal candidiasis). They may also be used in the treatment of systemic fungal infections caused by, for example, *Candida albicans, Cryptococcus neoformans, Aspergillus fumigatus,* Coccidiodes, Paracocciciodes, Histoplasma or Blastomyces spp. They may also be of use in treating eumycotic mycetoma, chromoblastomycosis and phycomycosis.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For the treatment of these conditions and diseases caused by immmunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 g per patient per day, assuming a 70 kg patient). In addition, the compounds of the present invention may be administered on an intermittent basis; i.e. at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

42-Allyloxy-rapamycin

To a solution of rapamycin (100 mg in 3.0 ml 33% methylene chloride in cyclohexane) is added allyl trichloroacetimidate (88 µL neat) and the reagents allowed to mix for 5 minutes. At this time, trifluoromethanesulfonic acid (4.5 µL neat) is added slowly via syringe and the mixture stirred at room temperature. After 18 hours the reaction is quenched by the addition of saturated sodium bicarbonate and extracted with ethyl acetate (3×5 mL). The combined organics are washed with brine and dried over magnesium sulfate. Purification of the concentrate by flash chromatography on silica gel gives the little compound.

EXAMPLE 5

42-(2', 3'-Dihydroxypropyloxy)-rapamycin

To the solution of 42-allyloxy-rapamycin (750 mg in 40 mL of tetrahydrofuran) is added 0.8 mL distilled water, followed by 1.2 g of 4-methylmorpholine-N-oxide hydrate and the mixture stirred at room temperature. After 15 minutes, osmium tetraoxide (1.16 mL of a 0.25M solution in THF) is added. The reaction is quenched after 2 hours by the addition of a 20% sodium bisulfite solution. Ethyl acetate is added and the layers are separated. The organic portion is re-extracted with 20% sodium bisulfite (3×20 mL) then washed with a saturated brine solution and dried over sodium sulfate. Purification of the concentrate by flash chromatography on silica gel gives the desired product.

EXAMPLE 3

42-Ethanoloxy-rapamycin

To a solution of 42-(2', 3'-dihydroxypropyloxy)-rapamycin (200 mg in 5 mL 25% aqueous tetrahydrofuran) is added sodium metaperiodate (70 mg) and the mixture stirred vigorously. After 4 hours the mixture is diluted with ethyl acetate and extracted from half-saturated sodium bicarbonate. The organic portion is dried over magnesium sulfate and purified by flash chromatography to give the desired product.

EXAMPLE 4

42-(4'-Phenyl-2'-imidazolylmethyloxy)-rapamycin

To a solution of 42-ethanyloxy-rapamycin (40 mg in 0.75 mL methanol) is added phenylglyoxal monohydrate (20 mg) followed by ammonium hydroxide 150 µL of a 58% water solution) and the mixture stirred at room temperature. After 15 hours, the solution is concentrated in vacuo and the mixture purified by flash chromatography on silica gel to give the title compound.

EXAMPLE 5

T-cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture um and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 105 heat-inactivated fetal calf serum, 100 mM glutamine, 1 mM sodium pyruvate, $2 \times 10^{-5}$M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4''-hydroxy-3-''-methoxycyclohexyl)-1'-methylvinyl]-23,25-dimethoxy-13,19,21,27-tetramethyl-11,28-dioxa-4-aza-tricyclo[22.3.1.0$^{4,9}$]-octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as concentration of compound required to inhibit tritiated thymidine uptake of T-cells by 50%.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

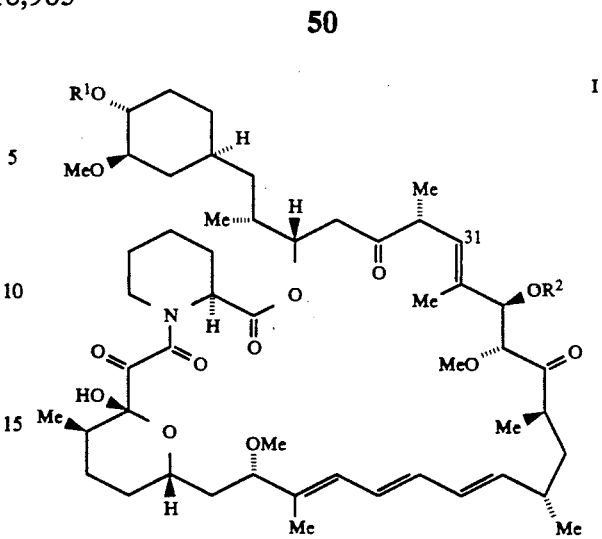

or a pharmaceutically acceptable salt thereof, wherein: $R^1$ is selected from the group consisting of:

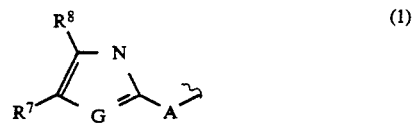

wherein G is N—$R^6$, O, S, SO, or $SO_2$,

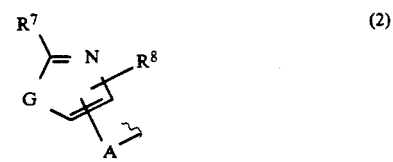

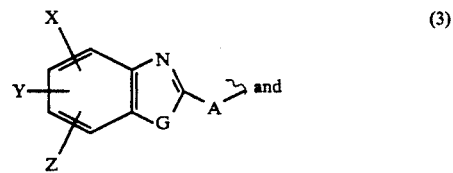

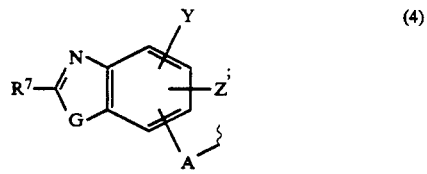

$R^2$ is independently selected from:
(1) the definitions of $R^1$;
(2) hydrogen;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl;
(8) substituted biphenyl in which the substituents are X, Y and Z;
(9) $C_{1-10}$alkyl;
(10) substituted $C_{1-10}$alkyl in which one or more substituent(s) is(are) selected from:

(a) hydroxy,
(b) oxo,
(c) $C_{1-6}$-alkoxy,
(d) phenyl-$C_{1-3}$alkoxy,
(e) substituted phenyl-$C_{1-3}$-alkoxy, in which the substituents on phenyl are X, Y and Z,
(f) —OCO—$C_{1-6}$alkyl,
(g) —$NR^9R^{10}$, wherein $R^9$ and $R^{10}$ are independently selected from:
  (i) hydrogen, or
  (ii) $C_{1-6}$alkyl unsubstituted or substituted with one or more of the substituent(s) selected from:
    (a') phenyl, which may be substituted with X, Y and Z,
    (b') —OH,
    (c') $C_{1-6}$alkoxy,
    (d') —$CO_2H$,
    (e') —$CO_2$—$C_{1-6}$alkyl,
    (f') —$C_{3-7}$cycloalkyl, and
    (g') —$OR^{11}$,
  (iii) or where $R^9$ and $R^{10}$ and the N to which they are attached may form a heterocyclic ring selected from the group consisting of: morpholine, thiomorpholine, piperidine, and piperazine,
(h) —$NR^9CO$—$C_{1-6}$alkyl—$R^{10}$, wherein $R^9$ and $R^{10}$ are as defined above,
(i) —$COOR^9$, wherein $R^9$ is as defined above,
(j) —CHO,
(k) phenyl,
(l) substituted phenyl in which the substituents are X, Y and Z,
(m) 1- or 2-napthyl,
(n) substituted 1- or 2-naphthyl in which the substituents are X, Y and Z,
(o) biphenyl,
(p) substituted biphenyl in which the substituents are X, Y and Z,
(q) —$OR^{11}$, and
(r) —$S(O)_p$—$C_{1-6}$alkyl;
(11) $C_{3-10}$alkenyl;
(12) substituted $C_{3-10}$alkenyl in which one or more substituent(s) is(are) selected from:
(a) hydroxy,
(b) oxo,
(c) $C_{1-6}$-alkoxy;
(d) phenyl-$C_{1-3}$alkoxy;
(e) substituted phenyl-$C_{1-3}$alkoxy, in which the substituents on phenyl are X, Y and Z,
(f) —OCO—$C_{1-6}$alkyl,
(g) —$NR^9R^{10}$, wherein $R^9$ and $R^{10}$ are as defined above,
(h) —$NR^9CO$—$C_{1-6}$alkyl, wherein $R^9$ is as defined above,
(i) —$COOR^9$, wherein $R^9$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z;
(q) —$OR^{11}$, and
(r) —$S(O)_p$—$C_{1-6}$alkyl;
(13) $C_{3-10}$alkynyl;
(14) substituted $C_{3-10}$alkynyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$-alkoxy, in which the substituents on phenyl are X, Y and Z,
(f) —OCO—$C_{1-6}$alkyl,
(g) —$N^9R^{10}$, wherein $R^9$ and $R^{10}$ are as defined above,
(h) —$NR^9CO$—$C_{1-6}$-alkyl, wherein $R^9$ is as defined above,
(i) —$COOR^9$, wherein $R^9$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —$OR^{11}$; and
(15) —$R^{11}$;
$R^6$ is selected from the group consisting of:
(1) hydrogen,
(2) $C_{1-6}$-alkyl, unsubstituted or substituted with:
  (a) hydroxy,
  (b) $C_{1-6}$alkoxy,
  (c) —$N^{12}R^{13}$, wherein $R^{12}$ and $R^{13}$ are independently selected from
    (i) hydrogen,
    (ii) $C_{1-6}$alkyl, or
    (iii) $C_{3-6}$alkenyl,
  (d) phenyl, unsubstituted or substituted with X, Y and Z,
  (e) —$OR^{11}$,
(3) $C_{3-6}$alkenyl, unsubstituted or substituted with:
  (a) hydroxy,
  (b) phenyl, unsubstituted or substituted with X, Y and Z, or
  (c) $C_{1-6}$alkoxy,
(4) phenyl, unsubstituted or substituted with X, Y and Z,
(5) —$R^{11}$,
(6) X, Y or Z;
$R^7$ and $R^8$ independently are selected from the group consisting of:
(1) hydrogen,
(2) $C_{1-7}$alkyl,
(3) $C_{2-6}$alkenyl,
(4) —$(CH_2)_m$—$NR^9R^{10}$, wherein $R^9$ and $R^{10}$ are as defined above, and m is 0, 1, 2, and 3,
(5) —$CF_3$,
(6) —$CONR^9R^{10}$, wherein $R^9$ and $R^{10}$ are as defined above,
(7) $R^{14}O(CH_2)_m$— wherein $R^{14}$ is hydrogen, $C_{1-6}$alkyl, hydroxy—$C_{2-3}$alkyl, —$CF_3$, phenyl, $R^{11}$ or naphthyl and m is as defined above,
(8)

wherein $R^{14}$ and m are as defined above;

(9) phenyl—$(CH_2)_m$— wherein m is as defined above and the phenyl is unsubstituted or substituted with X, Y and Z,

(10) napthyl—$(CH_2)_m$— wherein m is as defined above and the napthyl is unsubstituted or substituted with X, Y and Z,

(11) biphenyl—$(CH_2)_m$— wherein m is as defined above and the biphenyl is unsubstituted or substituted with X, Y and Z,

(12) heteroaryl—$(CH_2)_m$— wherein heteroaryl is selected from: acridine, carbazole, cinnoline, dibenzofuran, dibenzothiophene, quinozaline, pyrrazole, indole, imidazole, benzatriazole, furan, benzofuran, quinoline, isoquinoline, pyrazine, pyridazine, pyridine, pyrimidine, and pyrrole, m is as defined above and the heteroaryl is unsubstituted or substituted with X, Y, and Z,

(13) morpholinyl, and

(14) —CH=CH—phenyl wherein the phenyl is unsubstituted or substituted with X, Y and Z;

$R^{11}$ is selected from:

(a) —PO(OH)O⁻M⁺, wherein M⁺ is a positively charged inorganic or organic counterion, selected from the group consisting of: ammonium, sodium, lithium, potassium, calcium, magnesium, dicyclohexylamine, N-methyl-D-glucamine, arginine and lysine, (b) —$SO_3^-M^+$, (c) —$CO(CH_2)_qCO_2^-M^+$, wherein q is 1 to 3, and (d) —CO—$C_{1-6}$alkyl—$NR^9R^{10}$, wherein $R^9$ and $R^{10}$ are as defined above and the alkyl is unsubstituted or substituted with one or more substituents selected from:
  (i) hydrogen,
  (ii) $C_{1-6}$alkoxy,
  (iii) —$NR^{12}R^{13}$, wherein $R^{12}$ and $R^{13}$ are as defined above,
  (iv) —$COOR^6$, wherein $R^6$ is as defined above,
  (v) phenyl,
  (vi) substituted phenyl in which the substituents are X, Y and Z,
  (vii) imidazolidyl,
  (viii) indolyl,
  (ix) —SH, and
  (x) —S—$C_{1-6}$alkyl;

A is selected from the group consisting of:
(1) a bond,
(2) $C_{1-10}$alkyl;
(3) substituted $C_{1-10}$alkyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^9R^{10}$, wherein $R^9$ and $R^{10}$ are as defined above,
  (h) —$NR^9CO$—$C_{1-6}$alkyl, wherein $R^9$ is as defined above,
  (i) —$COOR^9$, wherein $R^9$ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —$OR^{11}$, and
  (r) —$S(O)_p$—$C_{1-6}$alkyl;

(4) —$C_{1-10}$alkyl wherein one or more of the alkyl carbons is replaced by a group selected from: —$NR^9$—, —O—, —$S(O)_p$—, —$CO_2$—, —$O_2C$—, —$CONR^9$—, —$NR^9CO$—, —$NR^9CONR^{10}$—;

(5) —$C_{3-10}$alkenyl wherein alkenyl contains one to four double bonds and wherein one or more of the alkyl carbons is replaced by a group selected from: —$NR^9$—, —O—, —$S(O)_n$—, —$CO_2C$—, —$CONR^9$—, —$NR^9CO$—, and —$NR^9CONR^{10}$—;

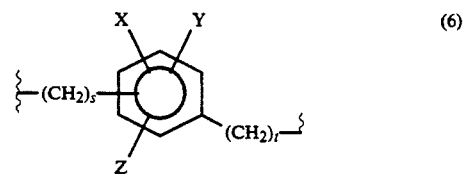

(6)

wherein s is 0 to 6 and t is 0 to 6,

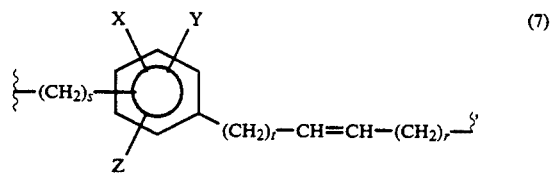

(7)

wherein r is 1 to 3 and s, and t are as defined above; X, Y and Z are independently selected from the group consisting of:

(a) hydrogen,
(b) $C_{1-10}$alkyl, unsubstituted or substituted with one or more substituents selected from:
  (i) aryl, wherein aryl is selected from the group consisting of phenyl and naphthyl,
  (ii) substituted aryl wherein aryl is as defined above and in which the substituents are X', Y' and Z',
  (iii) heteroaryl, wherein heteroaryl is as defined above,
  (iv) substituted heteroaryl wherein heteroaryl is defined above in which the substituents are X', Y', and Z',
  (v) unsubstituted or substituted aryloxy, wherein aryl is as defined above and in which the substituents on aryl are X', Y' and Z',
  (vi) —$OR^9$,
  (vii) —$OR^{11}$,
  (viii) —$OCOR^9$,
  (ix) —$OCO_2R^9$,
  (x) —$NR^9R^{10}$,
  (xi) —CHO,
  (xii) —$NR^9COC_{1-6}alkyl$-$R^{10}$,
  (xiii) —$NR^9CO_2C_{1-6}alkyl$-$R^{10}$,
  (xiv) —$NR^9CONR^9R^{10}$,
  (xv) —$OCONR^9R^{10}$,
  (xvi) —$CONR^9R^{10}$,
(c) $C_{1-10}$alkyl wherein one or more of the alkyl carbons is replaced by a group selected from —$NR^9$—, —O—, —$S(O)_p$—, —$CO_2$—, —$O_2C$—, —CONR⁹—, —NR⁹CO—, —NR⁹CONR¹⁰—, —CO—, —CH(OH)—, alkenyl or alkynyl and the alkyl may be unsubstituted or substituted with one or more substituents selected from:
(i) aryl, wherein aryl is as defined above,
(ii) substituted aryl wherein aryl is as defined above and in which the substituents are X', Y' and Z',
(iii) heteroaryl, wherein heteroaryl is as defined above,
(iv) substituted heteroaryl wherein heteroaryl is as defined above and in which the substituents are X', Y', and Z',
(v) unsubstituted or substituted aryloxy, in which the substituents on aryl are X', Y', and Z',
(vi) —OR⁹,
(vii) —OR¹¹,
(viii) —OCOR⁹,
(ix) —OCO₂R⁹,
(x) —NR⁹R¹⁰,
(xi) —CHO,
(xii) —NR⁹COC₁₋₆alkyl-R¹⁰,
(xiii) —NR⁹CO₂C₁₋₆alkyl-R¹⁰,
(xiv) —NR⁹CONR⁹R¹⁰,
(xv) —OCONR⁹R¹⁰,
(xvi) —CONR⁹R¹⁰,
(d) halogen,
(e) —NR⁹R¹⁰,
(f) —CN,
(g) —CHO,
(h) —CF₃,
(i) —SR¹⁵, wherein R¹⁵ is hydrogen, C₁₋₆alkyl, trifluoromethyl, or phenyl,
(j) —SOR¹⁵,
(k) —SO₂R¹⁵,
(l) —CONR⁹R¹⁰,
(m) R¹⁶O(CH₂)ₘ— wherein R¹⁶ is hydrogen, C₁₋₆alkyl, hydroxy-C₂₋₃alkyl, —CF₃, phenyl, R¹¹ or naphthyl and m is 0, 1, 2, or 3,
(n) —CH(OR¹⁷)(OR¹⁸), wherein R¹⁷ and R¹⁸ are C₁₋₃alkyl or taken together form an ethyl or propyl bridge,
(o)

wherein R¹⁶ and m are as defined above,
(p)

wherein R¹⁶ and m are as defined above, and
(q) —R¹¹;
or any two of X, Y and Z may be joined to form a saturated ring having 5, 6 or 7 ring atoms, said ring atoms comprising 1 or 2 oxygen atoms, the remaining ring atoms being carbon;
X', Y' and Z' independently are selected from:
(a) hydrogen,
(b) C₁₋₇alkyl,
(c) C₂₋₆alkenyl,
(d) halogen,
(e) —(CH₂)ₘ—NR⁹R¹⁰, wherein R⁹, R¹⁰ and m are as defined above,
(f) —CN, (g) —CHO,
(h) —CF₃,
(i) —SR¹⁵, wherein R¹⁵ is as defined above,
(j) —SOR¹⁵, wherein R¹⁵ is as defined above,
(k) —SO₂R¹⁵, wherein R¹⁵ is as defined above,
(l) —CONR⁹R¹⁰, wherein R⁹ and R¹⁰ are as defined above,
(m) R¹⁶O(CH₂)ₘ—, wherein R¹⁶ and m are as defined above,
(n) —CH(OR¹⁷)(OR¹⁸), wherein R¹⁷ and R¹⁸ are as defined above,
(o)

wherein R¹⁶ and m are as defined above,
(p)

wherein R¹⁶ and m are as defined above, and
(q) —R¹¹.
2. The compound of claim 1 wherein:
R¹ is selected from:

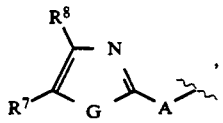

wherein G is N—R⁶, O, or S,

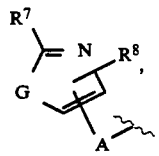

(2)

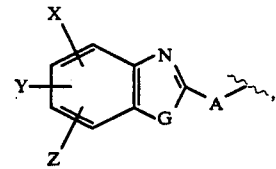

(3)

and

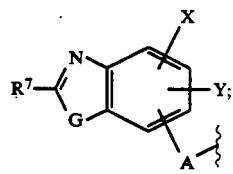

(4)

R² is independently selected from:
(1) hydrogen;
(2) phenyl;
(3) substituted phenyl in which the substituents are X, Y and Z;
(4) C₁₋₁₀alkyl;
(5) substituted C₁₋₁₀alkyl in which one or more substituent(s) is(are) selected from:

(a) hydroxy,
(b) $C_{1-6}$alkoxy,
(c) phenyl-$C_{1-3}$alkoxy,
(d) substituted phenyl-$C_{1-3}$alkoxy, in which the substituents on phenyl are X, Y and Z,
(e) —OCO—$C_{1-6}$alkyl,
(f) —COOR$^{20}$, wherein R$^{20}$ is hydrogen or $C_{1-6}$ alkyl,
(g) —CHO,
(h) phenyl, and
(i) substituted phenyl in which the substituents are X, Y and Z,
(6) $C_{3-10}$alkenyl;
(7) substituted $C_{3-10}$alkenyl in which one or more substituent(s) is(are) selected from:
(a) hydroxy,
(b) $C_{1-6}$alkoxy,
(c) phenyl-$C_{1-3}$alkoxy,
(d) substituted phenyl-$C_{1-3}$alkoxy, in which the substituents on phenyl are X, Y and Z,
(e) —OCO—$C_{1-6}$alkyl,
(f) —COOR$^{20}$, wherein R$^{20}$ is as defined above,
(g) —CHO,
(h) phenyl, and
(i) substituted phenyl in which the substituents are X, Y and Z,
(8) $C_{3-10}$alkynyl;
(9) substituted $C_{3-10}$alkenyl in which one or more substituent(s) is(are) selected from:
(a) hydroxy,
(b) $C_{1-6}$alkoxy,
(c) phenyl-$C_{1-3}$alkoxy,
(d) substituted phenyl-$C_{1-3}$alkoxy, in which the substituents on phenyl are X, Y and Z,
(e) —OCO—$C_{1-6}$alkyl,
(f) —COOR$^9$, wherein R$^9$ is as defined above,
(g) —CHO,
(h) phenyl,
(i) substituted phenyl in which the substituents are X, Y and Z; and
(10) —R$^{11}$;
R$^6$ is selected from the group consisting of:
(1) hydrogen;
(2) $C_{1-6}$alkyl, unsubstituted or substituted with:
(a) hydroxy,
(b) $C_{1-6}$alkoxy,
(c) phenyl, substituted or unsubstituted with X, Y and Z,
(d) —OR$^{11}$,
(3) $C_{3-6}$alkenyl, unsubstituted or substituted with:
(a) hydroxy,
(b) phenyl, unsubstituted or substituted with X, Y and Z, or
(c) $C_{1-6}$alkoxy, and
(4) phenyl, unsubstituted or substituted with X, Y and Z,
(5) —R$^{11}$,
(6) X, Y or Z;
R$^7$ and R$^8$ independently are selected from the group consisting of:
(1) hydrogen;
(2) $C_{1-7}$alkyl,
(3) $C_{2-6}$alkenyl,
(4) —CF$_3$,
(5) R$^{14}$O(CH$_2$)$_m$— wherein R$^{14}$ is hydrogen, $C_{1-6}$alkyl, hydroxy-$C_{2-3}$alkyl, —CF$_3$, phenyl, R$^{11}$ or naphthyl and m is 0, 1, 2 or 3
(6)

wherein R$^{14}$ and m are as defined above;
(7) phenyl-(CH$_2$)$_m$— wherein m is as defined above and the phenyl is unsubstituted or substituted with X, Y and Z,
(8) heteroaryl—(CH$_2$)$_m$— wherein heteroaryl is selected from: acridine, carbazole, cinnoline, dibenzofuran, dibenzothiophene, quinozaline, pyrrazole, indole, imidazole, benzotriazole, furan, benzofuran, quinoline, isoquinoline, pyriazine, pyridazine, pyridine, pyrimidine, and pyrrole, m is as defined above and the heteroaryl is unsubstituted or substituted with X, Y and Z, and
(9) —CH=CH—phenyl wherein the phenyl is unsubstituted or substituted with X, Y and Z;
R$^{11}$ is selected from:
(a) —PO(OH)O$^-$M$^+$, wherein M$^+$ is a positively charged inorganic or organic counterion, selected from the group consisting of: ammonium, sodium, lithium, potassium, calcium, magnesium, dicyclohexylamine, N-methyl-D-glucamine, arginine and lysine,
(b) —SO$_3^-$M$^+$,
(c) —CO(CH$_2$)$_q$CO$_2^-$M$^+$, wherein q is 1 to 3, and
(d) —CO—$C_{1-6}$alkyl-NR$^{20}$R$^{21}$, wherein R$^{20}$ is as defined above and R$^{21}$ is selected from the definitions of R$^{20}$;
A is selected from the group consisting of:
(1) a bond,
(2) $C_{1-10}$alkyl, and
(3)

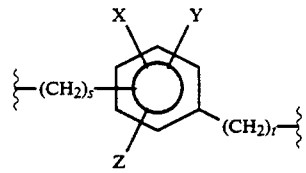

wherein s is 0 to 2 and t is 0 to 2;
X, Y and Z are independently selected from the group consisting of:
(a) hydrogen;
(b) $C_{1-7}$alkyl,
(c) $C_{2-6}$alkenyl,
(d) halogen,
(e) —(CH$_2$)$_m$—NR$^{20}$R$^{21}$, wherein R$^{20}$, R$^{21}$ and m are as defined above,
(f) —(CH$_2$)$_m$—CONR$^{20}$R$^{21}$, wherein R$^{20}$, R$^{21}$ and m are as defined above,
(g) —(CH$_2$)$_m$—NR$^{20}$—COR$^{14}$, wherein R$^{14}$, R$^{20}$ and m are as defined above,
(h) —O—(CH$_2$)$_m$—CONR$^{20}$R$^{21}$, wherein R$^{20}$, R$^{21}$ and m are as defined above,
(i) —CN,
(j) —CHO,
(k) —CF$_3$,
(l) R$^{14}$O(CH$_2$)$_m$— wherein R$^{14}$ and m are as defined above,
(m) —R$^{11}$.
3. The compound of claim 1 wherein:
R$^1$ is:

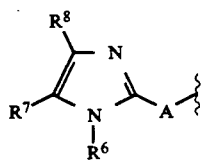

R[2] is hydrogen or methyl;

R[6] is hydrogen, methyl, benzyl, 3-fluorobenzyl, R[11] or —C$_{1-4}$ alkyl-OR[11];

R[7] and R[8] are independently selected from hydrogen, methyl, CH$_3$OCH$_2$—, HOCH$_2$—, phenyl, 3,5-difluorophenyl, 3-fluorophenyl, 3,4-difluorophenyl, 3,5-dichlorophenyl, 3-methoxyphenyl, 3-trifluoromethylphenyl, 3-hydroxyphenyl, 4-hydroxyphenyl, 3,5-dihydroxyphenyl 4-tert-butylphenyl, 3,4-methylenedioxyphenyl, 3,5-trifluoromethylphenyl, 4-methoxyphenyl, 3,5-dimethoxyphenyl, 3-trifluoromethoxyphenyl, 3,5-di(trifluoromethoxy)phenyl, 2-methoxyphenyl, 3-isopropyloxyphenyl, 3-ethoxyphenyl, 3,5-diethoxyphenyl, 3,4,5-trimethoxyphenyl, 3-hydorxyethyloxyphenyl, 3-propyloxyphenyl, 3-isobutyloxyphenyl, 3-methylphenyl, 3,5-dimethylphenyl, 3-ethylphenyl, 3,5-diethylphenyl, and phenylethyl;

A is —CH$_2$—, phenyl, or benzyl;

and pharmaceutically acceptable salts thereof.

4. A compound which is:

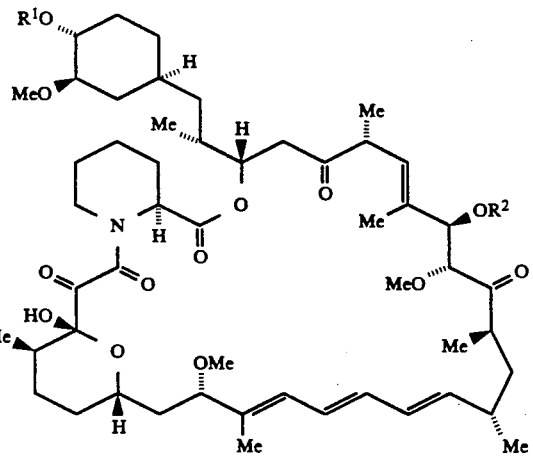

wherein R[1] and R[2] are selected from the following combinations of substituents:

| | R[1] | R[2] |
|---|---|---|
| (a) | ![pyrrole-imidazole] | H |
| (b) | CH$_3$-imidazole | H |
| (c) | phenyl-imidazole (NH) | H |
| (d) | phenyl-imidazole (NCH$_3$) | H |
| (e) | H | phenyl-imidazole (NH) |

-continued

| | R¹ | R² |
|---|---|---|
| (f) | 2-(1-methyl-4-phenylimidazol-2-yl)ethyl group | H |
| (g) | 2-(5-methyl-4-phenyl-1H-imidazol-2-yl)ethyl group | H |
| (h) | 2-(5-methoxymethyl-4-phenyl-1H-imidazol-2-yl)ethyl group | H |
| (i) | H | 2-(1-methyl-4-phenylimidazol-2-yl)ethyl group |
| (j) | H | 2-(5-methyl-4-phenyl-1H-imidazol-2-yl)ethyl group |
| (k) | H | 2-(5-methoxymethyl-4-phenyl-1H-imidazol-2-yl)ethyl group |
| (l) | 2-[4-(4-hydroxyphenyl)-1H-imidazol-2-yl]ethyl group | H |

-continued
| | R¹ | R² |
|---|---|---|
| (m) | 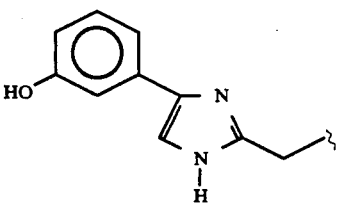 | H |
| (n) | 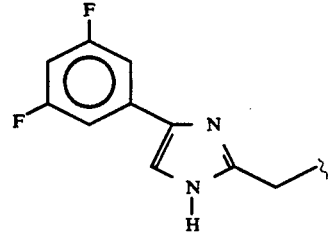 | H |
| (o) | H | 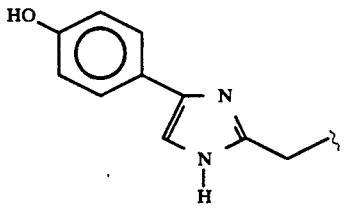 |
| (p) | H | 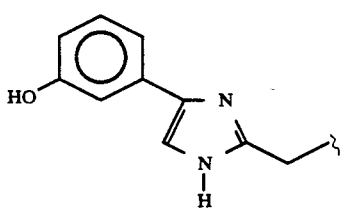 |
| (q) | H | 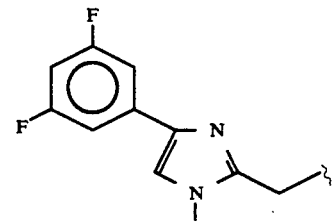 |
| (r) | 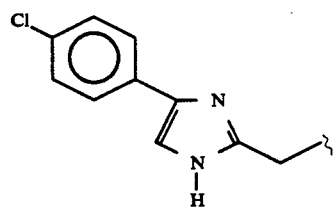 | H |
| (s) | H | 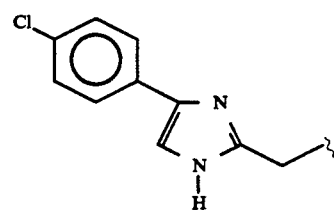 |

-continued
| | R¹ | R² |
|---|---|---|
| (t) | 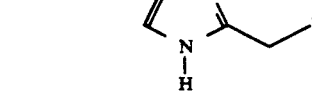 | H |
| (u) | H |  |
| (v) | 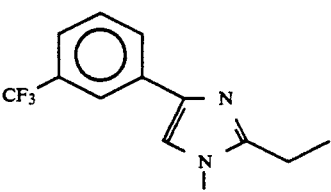 | H |
| (w) | 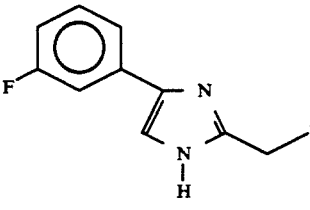 | H |
| (x) | 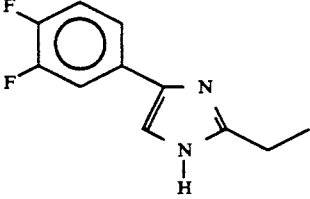 | H |
| (y) | 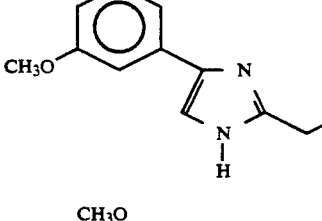 | H |
| (z) | 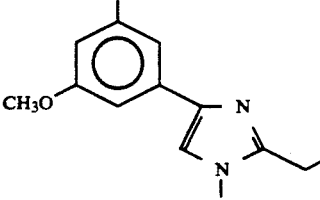 | H |

-continued
| | R[1] | R[2] |
|---|---|---|
| (aa) | H | 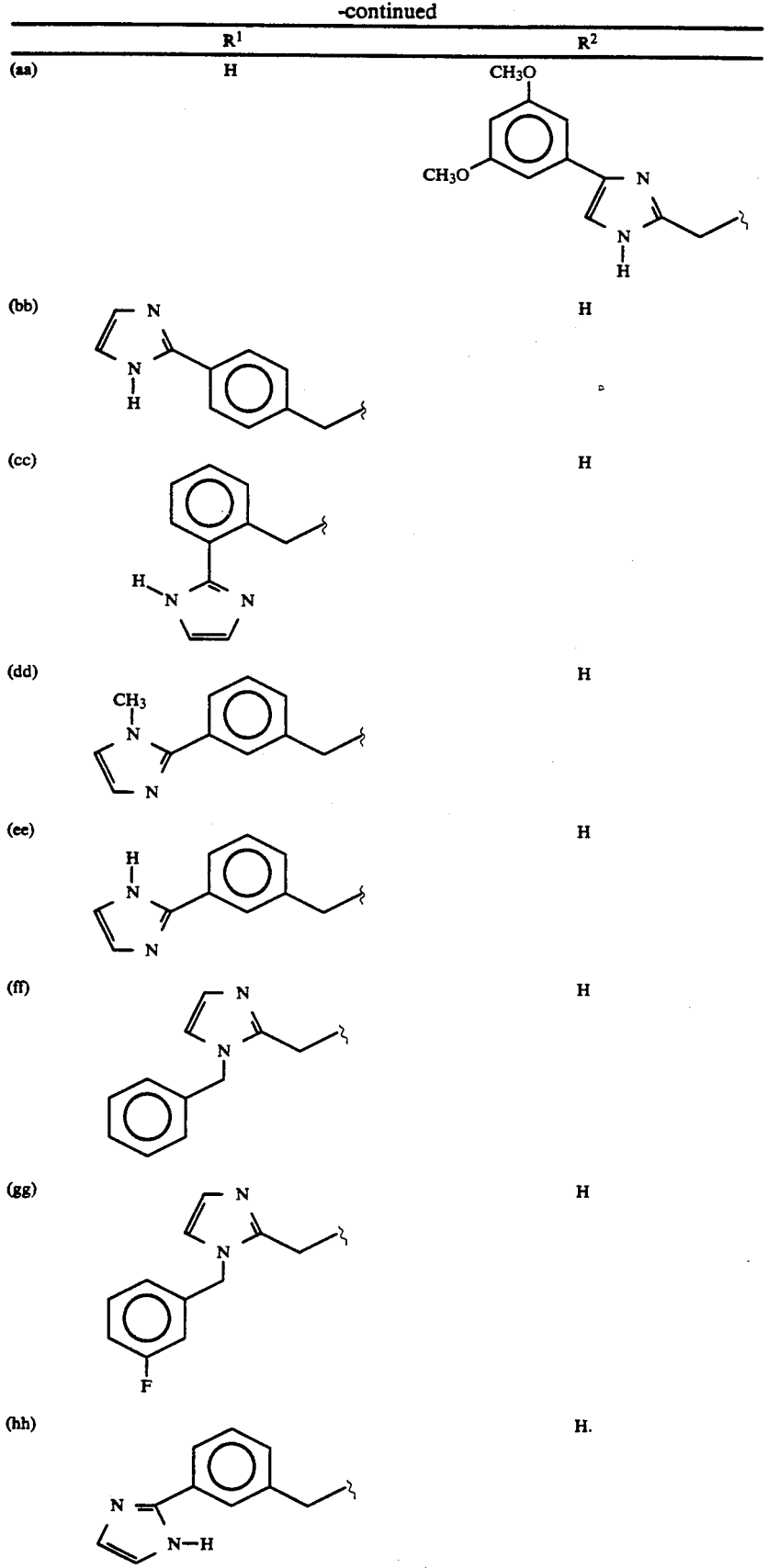 |
| (bb) | | H |
| (cc) | | H |
| (dd) | | H |
| (ee) | | H |
| (ff) | | H |
| (gg) | | H |
| (hh) | | H. |
5. A compound which is: 42-(4'-phenyl-2'-imidazoylymethyloxy)-rapamycin.